US009579676B1

(12) United States Patent
Burrowes et al.

(10) Patent No.: US 9,579,676 B1
(45) Date of Patent: Feb. 28, 2017

(54) DISPENSERS FOR MICROCAPSULES

(71) Applicant: The Procter & Gamble Company, Cincinnati, OH (US)

(72) Inventors: Lee Burrowes, Horsell (GB); William John Cleveland Connolly, Windlesham (GB); Alex Didier Milian, Les Baux de Breteuil (FR); Yannick Jacques Pointel, Epegard (FR)

(73) Assignee: The Procter & Gamble Company, Cincinnati, OH (US)

( * ) Notice: Subject to any disclaimer, the term of this patent is extended or adjusted under 35 U.S.C. 154(b) by 48 days.

(21) Appl. No.: 14/848,880

(22) Filed: Sep. 9, 2015

(51) Int. Cl.
  *B67D 7/70* (2010.01)
  *B05B 11/00* (2006.01)
  *A61L 9/14* (2006.01)

(52) U.S. Cl.
  CPC .............. *B05B 11/3081* (2013.01); *A61L 9/14* (2013.01); *B05B 11/3047* (2013.01)

(58) Field of Classification Search
  CPC ..... B05B 11/3081; B05B 11/3047; A61L 9/14
  USPC ......... 222/135–137, 94, 144.5, 145.1, 145.5, 222/183, 131, 162
  See application file for complete search history.

(56) References Cited

U.S. PATENT DOCUMENTS

| 3,236,418 A | 2/1966 | Dalle et al. |
| 3,488,004 A | 1/1970 | Peeps |
| 3,862,705 A * | 1/1975 | Beres ................... B65D 83/682 222/94 |

(Continued)

FOREIGN PATENT DOCUMENTS

| DE | 3911089 | 10/1990 |
| EP | 1 176 945 B1 | 11/2004 |

(Continued)

OTHER PUBLICATIONS

Patchan et al., Liquid-Filled Metal Microcapsules, The Johns Hopkins University, American Chemical Society, Applied Materials & Interfaces, 2012, 4, pp. 2406-2412.

(Continued)

*Primary Examiner* — Lien Ngo
(74) *Attorney, Agent, or Firm* — Betty J. Zea

(57) ABSTRACT

A dual dispenser having two pumps associated with a first and second receptacle and a common dispenser head, said common dispenser head having an output forming a dispensing orifice, said output channel being fed with the fluid products coming out of the two pumps, such that the two pumps have actuating rods that are movable axially over travel paths of different lengths, i.e. a first actuating rod having a long travel path and a second actuating rod having a short travel path; the common dispenser head has a pivoting member which forms two support elements for simultaneously moving the two actuating rods over an axial height corresponding to the short travel path, the support elements then continuing their movements by pivoting/ rotation of the pivoting member to finish the long travel path; wherein the first receptacle contains a first composition, the first composition including a volatile solvent and a first fragrance; wherein the second receptacle contains a second composition, the second composition including a carrier and a plurality of microcapsules; and methods relating thereto.

27 Claims, 4 Drawing Sheets

(56) References Cited

U.S. PATENT DOCUMENTS

| | | | |
|---|---|---|---|
| 4,773,562 A * | 9/1988 | Gueret | A45D 40/24 222/135 |
| 4,826,048 A | 5/1989 | Skorka et al. | |
| 4,969,579 A * | 11/1990 | Behar | B65D 83/682 222/1 |
| 5,152,461 A | 10/1992 | Proctor | |
| 5,169,029 A | 12/1992 | Behar et al. | |
| 5,332,157 A | 7/1994 | Proctor | |
| 5,901,883 A | 5/1999 | Ritsche | |
| 5,967,372 A * | 10/1999 | Favre | B05B 11/3084 222/137 |
| 6,082,588 A | 7/2000 | Markey et al. | |
| 6,189,810 B1 | 2/2001 | Nerushai et al. | |
| 6,454,135 B1 * | 9/2002 | Brozell | B05B 11/3011 222/135 |
| 6,626,379 B1 | 9/2003 | Ritsche et al. | |
| 6,655,551 B2 | 12/2003 | Manne | |
| 6,672,483 B1 | 1/2004 | Roy | |
| 6,722,532 B2 | 4/2004 | Lasserre et al. | |
| 6,869,027 B2 | 3/2005 | Foster et al. | |
| 6,978,946 B2 | 12/2005 | Sweeton | |
| 7,021,499 B2 | 4/2006 | Hansen et al. | |
| 7,335,631 B2 | 2/2008 | McDermott et al. | |
| 7,594,594 B2 | 9/2009 | Troost et al. | |
| 7,775,401 B2 | 8/2010 | Banco et al. | |
| 7,798,366 B2 | 9/2010 | Hoshino | |
| 7,819,342 B2 | 10/2010 | Spallek et al. | |
| 7,832,654 B2 | 11/2010 | Xu et al. | |
| 7,875,001 B2 | 1/2011 | Minotti | |
| 7,906,473 B2 | 3/2011 | Williams et al. | |
| 7,967,220 B2 | 6/2011 | Hansen et al. | |
| 7,997,449 B2 | 8/2011 | Banco et al. | |
| 8,002,151 B2 * | 8/2011 | Matthews | A47K 5/14 222/1 |
| 8,338,354 B2 | 12/2012 | Williams et al. | |
| 8,784,504 B2 | 7/2014 | Williams et al. | |
| 9,186,642 B2 | 11/2015 | Dihora et al. | |
| 9,303,820 B2 | 4/2016 | Miller | |
| 2004/0256490 A1 | 12/2004 | Sweeton | |
| 2005/0226900 A1 | 10/2005 | Winton Brooks et al. | |
| 2006/0205617 A1 | 9/2006 | Holzner et al. | |
| 2006/0207596 A1 | 9/2006 | Lane | |
| 2006/0258768 A1 | 11/2006 | Uchiyama et al. | |
| 2007/0278247 A1 * | 12/2007 | Banks | B05B 7/2497 222/132 |
| 2010/0091478 A1 | 4/2010 | Miller | |
| 2011/0186596 A1 | 8/2011 | Fontana | |
| 2013/0341356 A1 * | 12/2013 | Buell | A47K 5/14 222/135 |
| 2015/0351519 A1 | 12/2015 | Dring et al. | |
| 2015/0352575 A1 | 12/2015 | Dring et al. | |
| 2015/0352576 A1 | 12/2015 | Burrowes et al. | |
| 2015/0352577 A1 | 12/2015 | Burrowes et al. | |
| 2015/0352578 A1 | 12/2015 | Burrowes et al. | |
| 2015/0352579 A1 | 12/2015 | Burrowes et al. | |
| 2015/0353867 A1 | 12/2015 | Dring et al. | |
| 2015/0354550 A1 | 12/2015 | Burrowes et al. | |
| 2015/0375245 A1 | 12/2015 | Burrowes et al. | |

FOREIGN PATENT DOCUMENTS

| | | |
|---|---|---|
| FR | 2 669 243 B1 | 2/1993 |
| JP | 4464803 B2 | 5/2010 |

OTHER PUBLICATIONS

PCT International Search Report dated May 24, 2016—4 pages.

* cited by examiner

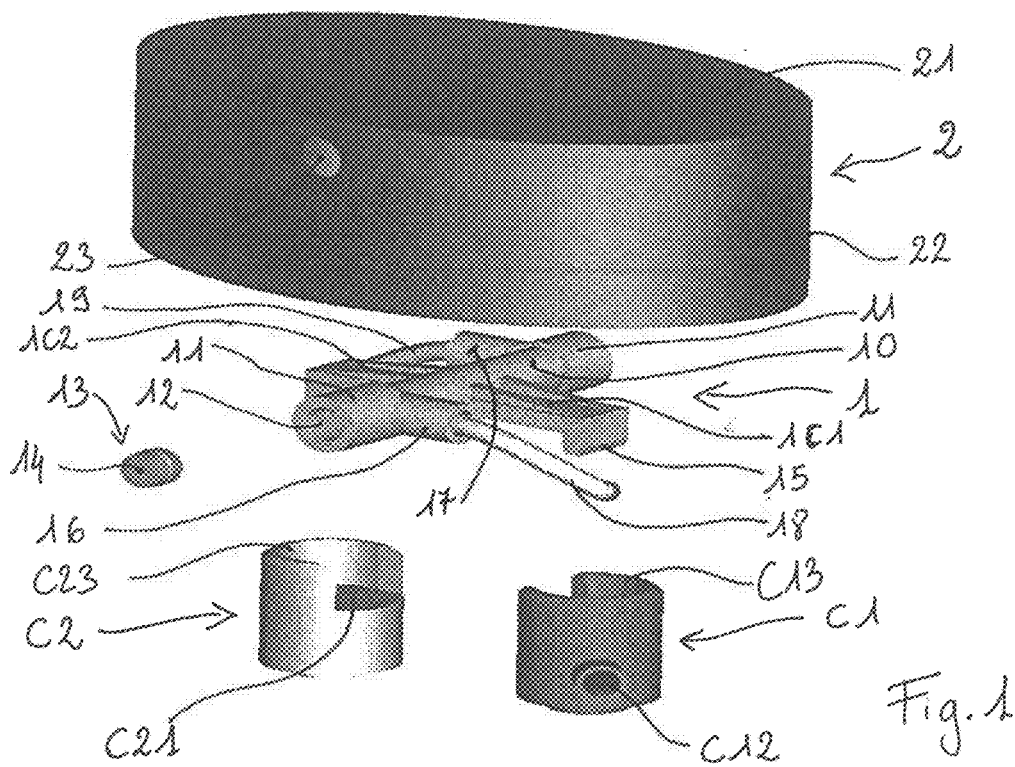
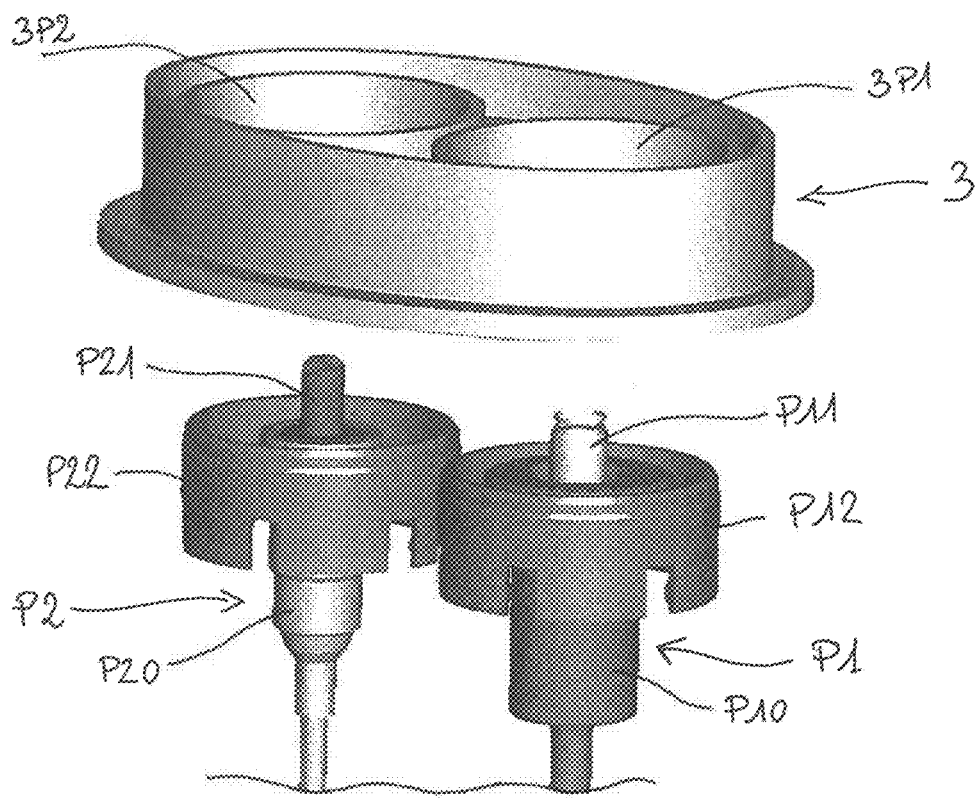
Fig. 1

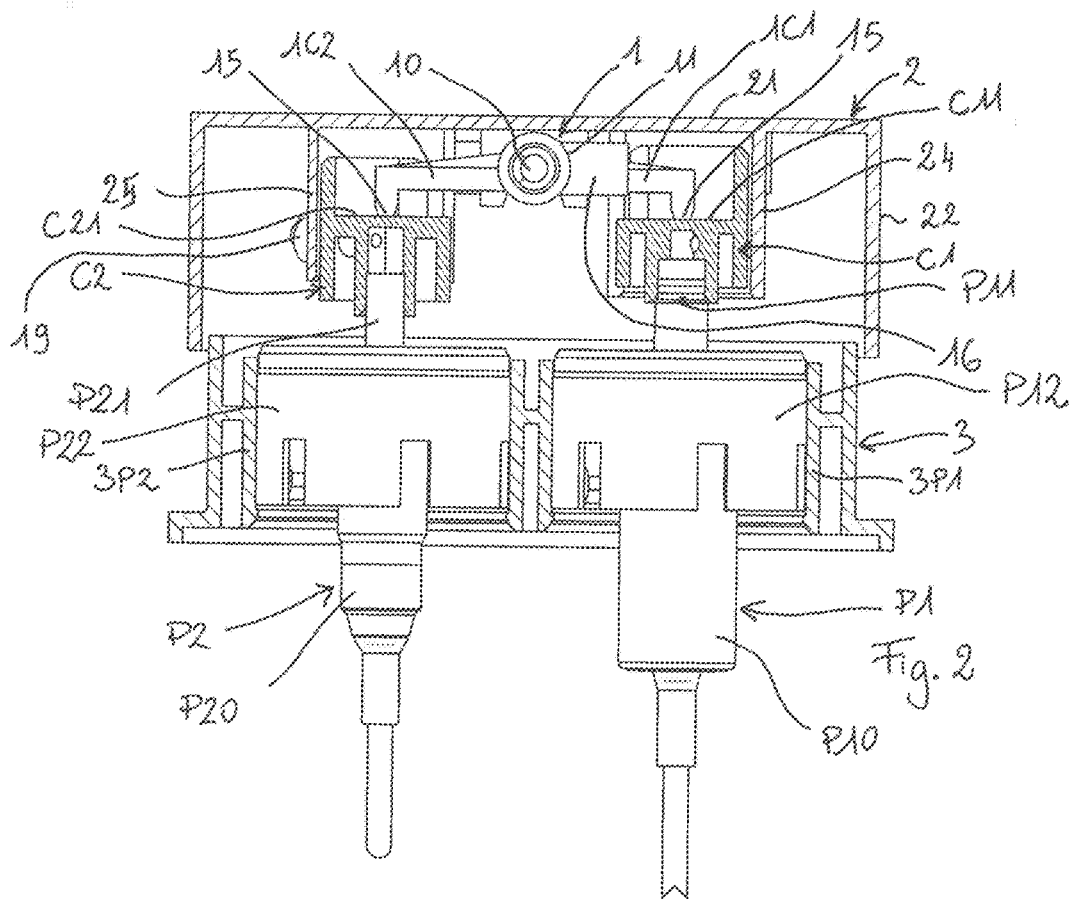
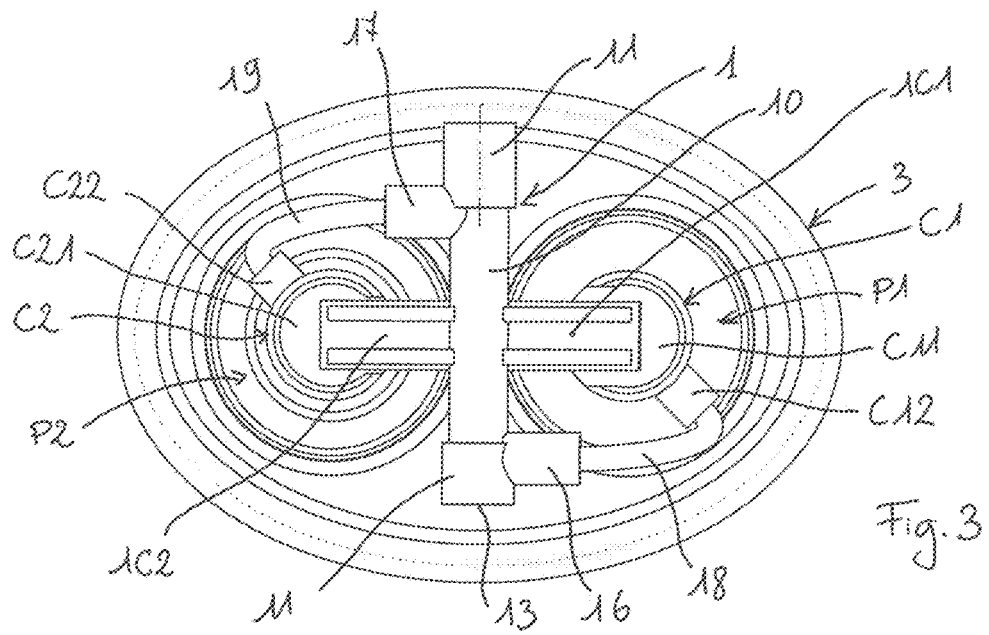

US 9,579,676 B1

DISPENSERS FOR MICROCAPSULES

TECHNICAL FIELD

The present disclosure generally relates to dispensers capable of dispensing microcapsules.

BACKGROUND

Consumers often desire to deliver pleasant fragrances during and/or after application of a product. Such fragrances often contain perfume oils and/or other odoriferous materials that provide a scent for a limited period of time. It is also not uncommon to include a solvent for solubilizing the perfumes oils and/or other odoriferous materials. At times, such solvents may be incompatible with other ingredients that may provide a benefit to the consumer. While dispensers that contain separate chambers for separating incompatible ingredients may exist, such dispensers may not provide a consistent experience to the consumer or may not be capable of dispensing certain ingredients without damaging and/or clogging the system. Thus, there exists a need for dispensers than can keep some incompatible ingredients separate while delivering a consistent experience to the consumer.

SUMMARY

A dual dispenser comprising a first pump (P1) in liquid communication with a first receptacle (R1), a second pump (P2) in liquid communication with a second receptacle (R2), and a common dispenser head, said common dispenser head comprising an output channel (10) forming a dispensing orifice (14), said output channel (10) being fed with a first and second composition coming out of the first and second pumps (P1, P2); wherein the first pump (P1) is operatively associated with a first actuating rod (P11) and the second pump (P2) is operatively associated with a second actuating rod (P21); wherein the first actuating rod (P11) has a longer travel path than the second actuating rod (P21); wherein the common dispenser head comprises a pivoting member (1) which forms two support elements (1C1, 1C2) for simultaneously moving the two actuating rods (P11, P21) over an axial height corresponding to the shorter travel path, the support elements (1C1, 1C2) then continuing their movements by pivoting/rotation of the pivoting member (1) to finish the longer travel path; wherein the first receptacle (R1) comprises the first composition, the first composition comprising a volatile solvent and a first fragrance; wherein the second receptacle (R2) comprises the second composition, the second composition comprising a carrier and a plurality of microcapsules.

A method of providing a longer lasting fragrance, the method comprising spraying the first and second composition using the aforementioned dual dispenser.

BRIEF DESCRIPTION OF THE DRAWINGS

While the specification concludes with claims, it is believed that the same will be better understood from the following description taken in conjunction with the accompanying drawings in which:

FIG. 1 is an exploded view in perspective of a dispenser disclosed herein, the two receptacles not being represented, FIG. 2 is a view in vertical cross-section through the dispenser of FIG. 1 in the assembled state and resting position, in the absence of receptacles, FIG. 3 is a cutaway top view of FIG. 2;

FIGS. 1 to 3 will be referred to independently in order to describe in detail the structure of a dual dispenser according to the invention capable of dispensing simultaneously two fluid products of different natures, textures and/or properties. An optional shell containing the two receptacles is also not represented.

DETAILED DESCRIPTION

Figure 4:
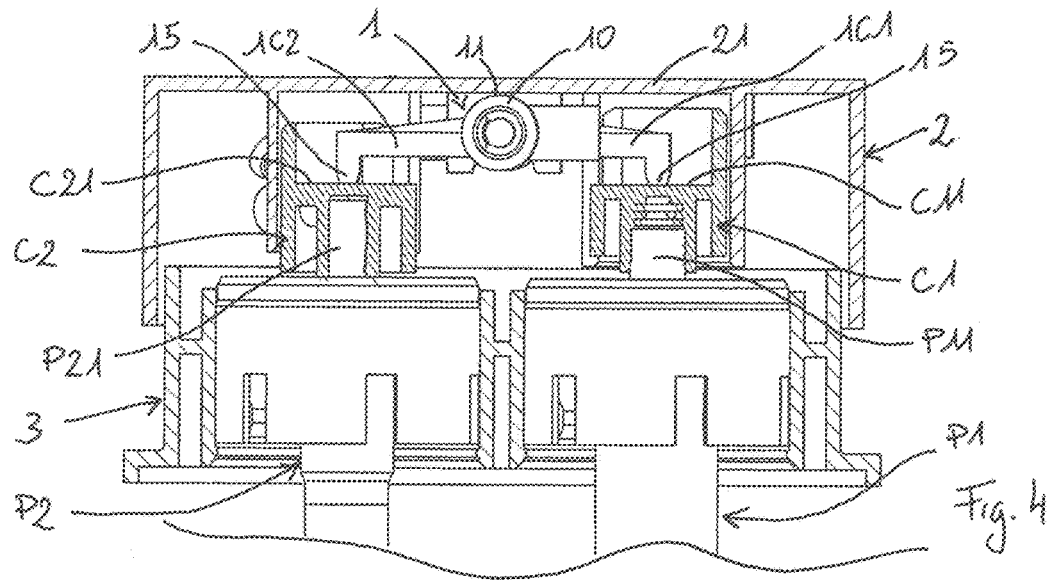
FIG. 4 is a view similar to the one in FIG. 2, with the dispenser head having completed the short travel path.

All percentages are weight percentages based on the weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither understood to be made at about 25° C. and at ambient conditions, where "ambient conditions" means conditions under about one atmosphere of pressure and at about 50% relative humidity.

"Composition" as used herein, means ingredients suitable for topical application on mammalian keratinous tissue. Such compositions may also be suitable for application to textiles or any other form of clothing including, but not limited to, clothing made from synthetic fibers like nylons and polyesters, and clothing made from acetate, bamboo, cupro, hemp, flannel, jute, lyocell, PVC-polyvinyl chloride, rayon, recycled materials, rubber, soy, Tyvek, cotton, and other natural fibers.

"Free of" means that the stated ingredient has not been added to the composition. However, the stated ingredient may incidentally form as a byproduct or a reaction product of the other components of the composition.

"Nonvolatile" refers to those materials that liquid or solid under ambient conditions and have a measurable vapor pressure at 25° C. These materials typically have a vapor pressure of less than about 0.0000001 mmHg, and an average boiling point typically greater than about 250° C.

"Soluble" means at least about 0.1 g of solute dissolves in 100 ml of solvent at 25° C. and 1 atm of pressure.

"Substantially free of" means an amount of a material that is less than 1%, 0.5%, 0.25%, 0.1%, 0.05%, 0.01%, or 0.001% by weight of a composition.

"Derivatives" as used herein, include but are not limited to, amide, ether, ester, amino, carboxyl, acetyl, and/or alcohol derivatives of a given chemical.

"Skin care actives" as used herein, means substances that when applied to the skin, provide a benefit or improvement to the skin. It is to be understood that skin care actives are useful not only for application to skin, but also to hair, nails and other mammalian keratinous tissue.

"Situs" means the location where the composition is applied. Non-limiting examples of a situs include mammalian keratinous tissue and clothing.

"Volatile," as used herein, unless otherwise specified, refers to those materials that are liquid or SOLID under ambient conditions and which have a measurable vapor pressure at 25° C. These materials typically have a vapor pressure of greater than about 0.0000001 mmHg, alternatively from about 0.02 mmHg to about 20 mmHg, and an average boiling point typically less than about 250° C., alternatively less than about 235° C.

Dispensers

The disclosure herein concerns a dual dispenser comprising two receptacles of different fluid products, two pumps and a common dispenser head, said common dispenser head comprising an output channel forming an output orifice, said output channel being fed with the fluid products from the two pumps.

Dual dispensers have long been known that are capable of dispensing two different fluid products from distinct receptacles through a single common dispensing orifice. Document FR2654016 is an example thereof. It describes a dual dispenser comprising a rotary wedge that is movable above the actuating rod of one of the pumps to vary the insertion of the actuating rod, thus varying the dose to be mixed with the dose dispensed by the other pump.

In contrast, the dispensers herein do not vary the dose dispensed by the pumps by acting on the course of travel of one of the actuating rods, but rather to dephase the dispensing of the fluid products at the end of travel, so that only one fluid product is dispensed through the dispensing orifice at the end of the dispensing phase. In other words, the dispensing orifice is only in contact with one fluid product after the dispensing phase, i.e. the dispensing orifice is only in contact with the two fluid products during the dispensing phases.

To achieve this end, the dispensers herein may comprise two pumps associated respectively with two receptacles of different fluid products and a common dispenser head, said common dispenser head comprising an output channel forming an output orifice, said output channel being fed with the fluid products from the two pumps, wherein:

the two pumps comprise actuating rods that are movable axially over travel paths of different lengths, i.e. a first actuating rod having a long travel path and a second actuating rod having a short travel path, the common dispenser head comprises a pivoting member which forms two support elements for simultaneously moving the two actuating rods over an axial height corresponding to the short travel path, the support elements then continuing their movements by pivoting/rotation of the pivoting member to terminate the long travel path.

Thus, the two support elements first travel, from the position of rest of the common dispenser head, over a travel path that is identical, symmetrical and synchronous, then, when the second actuating rod having a short travel path has been fully inserted, the support elements begin a pivoting/rotational movement of the pivoting member, so that the support element associated with the first actuating rod having a long travel path follows its axial trajectory until the first actuating rod is fully inserted. It is preferable for the actuating forces of the two actuating rods to be substantially or perfectly identical. Furthermore, axial guiding means must be provided that enable an identical, symmetrical and synchronous movement of the two support elements.

According to one advantageous characteristic, the two support elements are integral with each other in movement. Preferably, the two support elements are integral with the output channel. More preferably yet, the two support elements extend on either side of the output channel, advantageously symmetrically. The output channel can for example be rectilinear over at least part of its length, and the two support elements can extend symmetrically opposite from the channel.

According to another advantageous aspect, the two support elements pivot around the output channel. This induces a slight rotation of the output channel around its own axis, since it functions as a pivot axis for the two support elements.

According to another advantageous aspect, the pivoting member can comprise at least one thrust transmission zone, and advantageously two, so that an axial thrust exerted on said thrust transmission zone first causes the translatory movement of the two support elements and of the output channel over the short travel path, and then a slight rotation of the output channel around its own axis and the pivoting of the support elements to terminate the long travel path. In other words, the output channel and its two support elements are first moved translationally over the short travel path, then they pivot around the contact point of the support element which is stopped at the second fully inserted actuating rod. The support element associated with the first actuating rod continues its downward movement, not in a translatory manner, but rather describing an arc of circle the radius of which corresponds to the distance between the contact points of the two support elements. The output channel also describes a slight arc of circle, but with a smaller radius, i.e. half that of the support elements.

According to another advantageous characteristic, the common dispenser head comprises a cover which is in support contact on the thrust transmission zones. Advantageously, the output channel comprises a thrust transmission zone near each of its ends. Advantageously, the support elements extend substantially perpendicular to the output channel between the two thrust transmission zones. The formation of two thrust transmission zones makes it possible to distribute the thrust equally over the length of the output channel, and the fact of positioning the transmission zones at the ends of the channel makes it possible to maintain the channel perfectly stable during the movement thereof.

According to a very interesting aspect, the first actuating rod having the long travel path can be connected to the output channel closer to the dispenser orifice than the second actuating rod having the short travel path. Thus, the fluid product coming out of the first actuating rod (having a long travel path) will pass alone and last through the dispenser orifice during each dispensing phase, so that in the rest position, there is only fluid product coming out of the first actuating rod at the dispenser orifice. This is particularly advantageous when the fluid product coming out of the second actuating rod is sensitive, or can become denatured or can deteriorate in contact with air. By using a fluid product (coming out of the first actuating rod) that is more stable and/or with disinfecting or bactericidal properties, it is ensured that there will be no contaminated or altered residue of fluid product at the dispenser orifice.

In some examples, each actuating rod can be topped by a cap defining a support plate for its respective support element and a connector fitting receiving a flexible conduit which connects to the output channel. Said cap can simply be force fit onto the free end of the actuating rod.

The design of the dispensers disclosed herein rests on the principle of actuating both pumps by means of a rotational member which is moved first translationally over the path common to both pumps, then by rotation or pivoting to terminate the actuation of the pump which has the longest travel path. Thus, one of the pumps will dispense the fluid product after the other pump at the end of the dispensing phase in order to expose the dispensing orifice, and a section of the output channel, only to one fluid product, which will advantageously have stable, disinfecting and/or bactericidal properties.

Thus, the dual dispensers disclosed herein comprises two pumps P1 and P2 each comprising a pump body P10 and P20 as well as two actuating rods P11 and P21 which are axially movable back and forth in their respective pump bodies P10 and P20 against a return spring, not represented. The actuating rods P11 and P21, which project upwards out of the bodies P10 and P20, are movable over heights of different travel paths, i.e. a long travel path for the actuating rod P11 and a short travel path for the actuating rod P21. The pumps P1 and P2 each define a pump chamber of identical or different volumes.

Moreover, it can be advantageous for the actuating rods P11 and P21 to have substantially or perfectly identical resistance to insertion. Otherwise, it may require specific means to compensate for any difference in resistance to insertion of the two actuating rods. Each pump P1, P2 also comprises a retaining ring P12, P22 to mount the pump securely and sealably on the neck of a respective receptacle (not shown). The type of attachment is not critical and may vary.

The dual dispenser disclosed herein also comprises an opening 3 defining two housings 3P1 and 3P2, respectively for the pumps P1 and P2. As can be seen in FIG. 2, the retaining rings P12 and P22 fit tightly inside the two housings 3P1 and 3P2, in order to lock the rings onto the necks of the receptacles. This is a completely standard configuration in the domain of cosmetics. The opening 3 can cooperate with a shell (not shown) in which the two receptacles (not shown) are received.

The dual dispenser disclosed herein also comprises two caps C1 and C2 which respectively cover the free ends of the actuating rods P11 and P21, as can be seen in FIG. 2. The caps C1 and C2 can be identical, or slightly different, for example to be adapted to actuating rods of different diameters. Each cap C1, C2 comprises a support plate C11, C21 as well as a lateral connector fitting C12, C22. Said connector fitting communicates directly with the actuating rods P11, P21, in such a way that the fluid products forced through the actuating rods reach their two connector fittings C12, C22. The support plates C11, C21 extend substantially perpendicular to the axis of movement of the actuating rods P11, P21. Advantageously, each support plate is partially surrounded by an notched crown C13, C23.

The dual dispenser disclosed herein also comprises a pivoting member 1, which can advantageously be formed in one piece. Said pivoting member 1 comprises an output channel 10, which here has a rectilinear configuration. The output channel 10 is blocked at one of end, and at the other end thereof defines an opening 12 in which a spray nozzle 13 is inserted which defines a dispensing orifice 14. Thus, the fluid product that arrives in the output channel 10 exits therefrom through the dispensing orifice 14 of the spray nozzle 13 that blocks the opening 12. It will also be noted that the two ends of the channel 10 are reinforced so as to define two thrust transmission zones 11, as will be explained hereinafter. The output channel 10 comprises two connection fittings 16, 17, each of which receives a flexible conduit 18, 19 respectively connected to the connector fittings C12, C22 of the two caps C1 and C2. The flexible conduits 18 and 19 can be inserted into the fittings 16, 17, C12 and C22, or as a variant, can be produced from a single piece together with the pivoting member 1, or with the caps C1 and C2. It can be seen more clearly in FIG. 3 how the flexible conduits 18 and 19 connect to the fittings 16, 17, C12 and C22, while having an angled configuration. It can be noted in FIGS. 1 and 3 that the fitting 16 is disposed near the spray nozzle 13, and therefore near to the dispensing orifice 14, while the connection fitting 17 is situated near the end opposite to the spray nozzle 13. Consequently, the fluid product coming out of the pump P1 and travelling through the cap C1 and the flexible conduit 18 is injected into the output channel 10 in the immediate vicinity of the dispensing orifice 14. On the contrary, the fluid product coming out of the pump P2 must travel through the full length of the conduit of the output channel 10.

The pivoting member 1 also forms two support elements 1C1 and 1C2 that extend perpendicular, symmetrically and opposite to the output channel 10. It could be said that the output channel 10 and the two support elements 1C1 and 1C2 have a configuration that is generally cross shaped. As a result of this, the two support elements 1C1 and 1C2 are joined together by means of the output channel 10. Each support element has the shape of an elongated tab which defines at its free end a support head 15 which is oriented downwards, and which comes into contact with the support plate C11, C21 of the caps C1, C2, as shown in FIG. 2. The support elements 1C1 and 1C2 extend through the notches of the notched crowns C13 and C23 to allow their respective support heads 15 to come into contact with the support plates C11, C21. Advantageously, support heads 15 extend in line with the actuating rods P11, P21. It will also be noted that the support elements 1C1 and 1C2 are connected to the output channel 10 substantially midway between the two thrust transmission zones 11 situated at the two opposite ends of the channel 10.

The dual dispenser disclosed herein also comprises a cover 2, oval shaped in this instance, which defines an upper support surface 21 as well as a peripheral skirt 22 through which a hole 23 is made that will face the spray nozzle 13. The cover 2 also comprises a retaining bushing 24 in which the cap C1 is secured. Moreover, the cover 2 also comprises a guide bushing 25 that encloses the cap C2, while allowing it to slide inside. As can be seen in FIG. 2, the skirt 22 of the cover 2 extends around the opening 3 so as to completely conceal the caps C1, C2 as well as the dispensing and support member 1.

The two caps C1 and C2, the pivoting member 1 and the cover 2 together form the fluid products dispensing head, which is common to both pumps P1 and P2.

In FIG. 2, the dispenser is in its rest configuration, with both actuating rods P11 and P21 in their maximum extended position outside their respective pump bodies P10, P20. The two support plates C11 and C21 are situated substantially or perfectly at the same height. This is obviously also true for the two support heads 15 of the two support elements 1C1 and 1C2. The lower face of the support surface 21 of the cover 2 is in contact with the output channel 10 at the two thrust transmission zones 11. Starting from this rest position, the user presses with one or more fingers on the support surface 21 of the cover 2 with sufficient thrust force to move the cover 2 towards the opening 3. The thrust thus exerted on the cover 2 is transmitted to the output channel 10 at these two thrust transmission zones 11. The thrust force is then transmitted through the thrust elements 1C1 and 1C2 to the support heads 15 which are in contact supported on the support plates C11 and C21. The thrust is then transmitted to the actuating rods P11 and P21, which are thus forced to be inserted inside their respective pump bodies P10 and P20. Due to the fact that the actuating rods P11 and P21 have an identical or nearly identical resistance to insertion, and to the fact that the support elements 1C1 and 1C2 are symmetrically identical, the two actuating rods P11 and P21 are inserted simultaneously until the actuating rod P21, which has the shortest travel path, is completely inserted. This intermediate and instantaneous position is represented in FIG. 4. Both actuating rods P11 and P21 have then traveled the same distance, i.e. the short distance which is the maximum travel path of the actuating rod P21. The different fluid products coming out of both pumps P1 and P2 have then been conveyed simultaneously in parallel through their respective actuating rods P11, 21, their respective caps C1, C2, their respective flexible conduits 18, 19 to arrive in the output channel 10 where the two fluid products are mixed before being dispensed through the single common dispensing orifice 14. The simultaneous dispensing of the two fluid products has occurred from the resting configuration of FIG. 2 until the intermediate configuration of FIG. 4.

If the user continues exerting pressure on the support surface 21, the cover 2 will continue moving downwards, transmitting the thrust to the pivoting member 1 at the two thrust transmission zones 11 of the output channel 10. Because the head 15 of the support element 1C2 is blocked in position due to the actuating rod P21 being completely inserted, the thrust transmitted at the output channel 10 causes an additional downward movement of the support head 15 of the support element 1C1. This results in the actuating rod P11 being completely inserted so that it has completed its long travel path. Over the course of this additional travel path, the fluid product coming out of the pump P1 has been injected first into the output channel 10, then through the dispensing orifice 14. It should be noted that only the fluid product coming out of the pump P1 passes through the dispensing orifice 14 at the end of the dispensing phase, the dispensing of the other fluid product coming out of the pump P2 having been completed when the actuating rod P21 has completed its short travel path.

Figure 5:
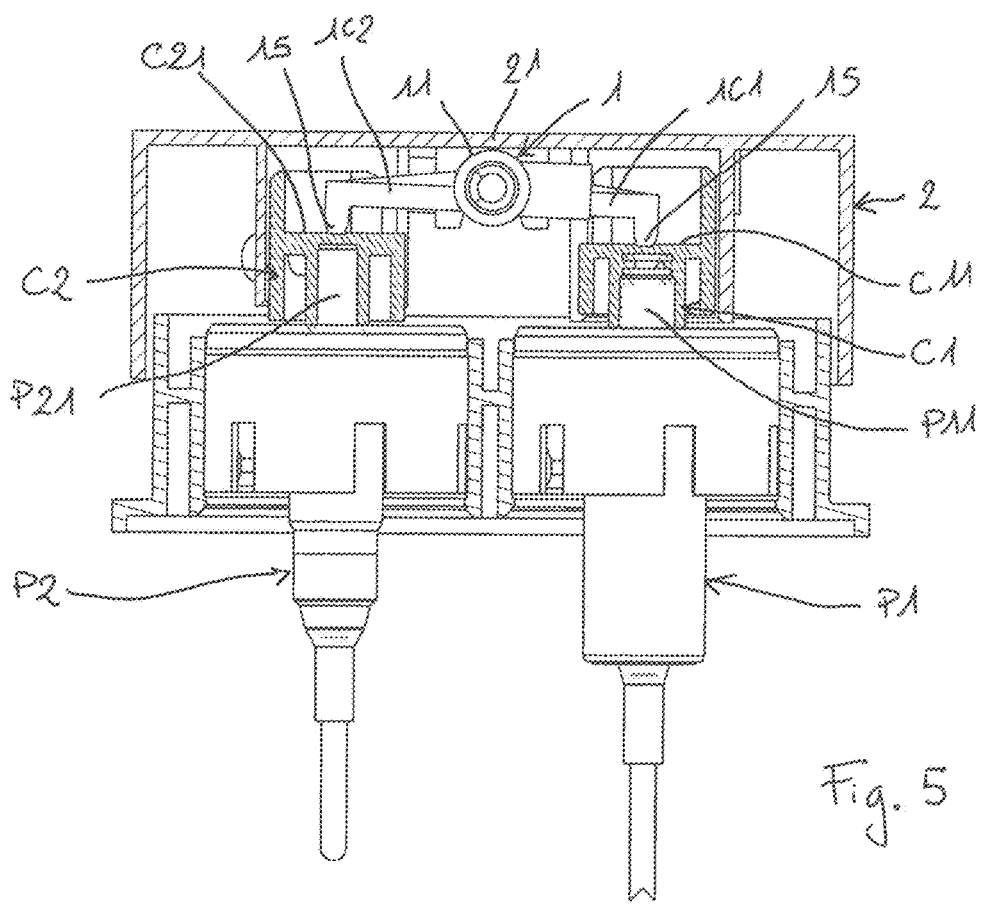
FIG. 5 is a view similar to the one in FIG. 4, with the dispenser head having completed the long travel path.

By comparing FIGS. 4 and 5, it can be seen that the orientation of the two support elements 1C1 and 1C2 has been modified. Indeed, in FIG. 4 the two support elements 1C1 and 1C2 are extended in a substantially horizontal plane, while in FIG. 5 the same support elements extend in a plane that is slightly inclined towards the right. Consequently, with reference to the cover 2, the support elements 1C1 and 1C2 have made a slight pivoting or rotational movement around the point of contact of the support head 15 against the support plate C21. This is also the case for the output channel 10 which has made a corresponding slight pivoting. In contrast, with reference to the output channel 10, it can be said that the output channel (10) has made a slight rotation around its own axis, and the support elements (1C1, 1 C2) have made a pivoting movement around the output channel (10) to finish the long travel path.

The fact that the pump P1 is the only to dispense the fluid product at the end of the dispensing phase makes it possible to eliminate the fluid product coming out of the pump P2 when the dispenser is in the resting position. Thus, the fluid product coming out of the pump P2 is only present in the dispensing orifice 14 during the dispensing phase, and then not in its entirety, since at the end of the dispensing phase only the product coming out of the pump P1 is passing through the dispensing orifice 14. It will then be recalled that the fluid product coming out of the pump P1 is injected into the output channel 10 near the spray nozzle 13, at the connection fitting 16, as can be seen in FIG. 3. This means that a very small quantity of fluid product coming out of the pump P1 is sufficient to eliminate the fluid product coming out of the pump P2 at the dispensing orifice 14, at the end of the dispensing phase. In the resting position as represented in FIG. 4, the fluid product coming out of the pump P2 fills nearly all of the output channel 10, except for its end near the spray nozzle 13.

The dual dispenser disclosed herein is particularly advantageous for dispensing two fluid products of different natures and/or properties. For example, the fluid product dispensed by the pump P2 can be a sensitive or easily degradable fluid product, while the fluid product dispensed by the pump P1 can be another fluid product that is more stable, more resistant or that has bactericidal or disinfectant properties. For example, it can be provided that the pump P1 distributes an alcoholic solution. Thus, at the end of each dispensing phase, the dispensing orifice 14 is cleaned by the passage of a small dosage of alcoholic solution that ensures a perfect cleaning of the spray nozzle 13.

In this regard, the dual dispenser disclosed herein may be used in order to prevent the buildup of residual damaged microcapsules within a dispenser. These residual microcapsules may in some cases promote clogging. The residual microcapsules may also leave an unsightly residue at or near the exit orifice that may be undesirable for a fine fragrance product. Without being limited by theory, it is believed that the concentration and type of microcapsule used may in some cases lead to a clogging of the dispenser. In some examples, pump P1 pumps a first composition containing a volatile solvent (e.g. ethanol) and pump P2 pumps a second composition containing microcapsules.

Figure 6:
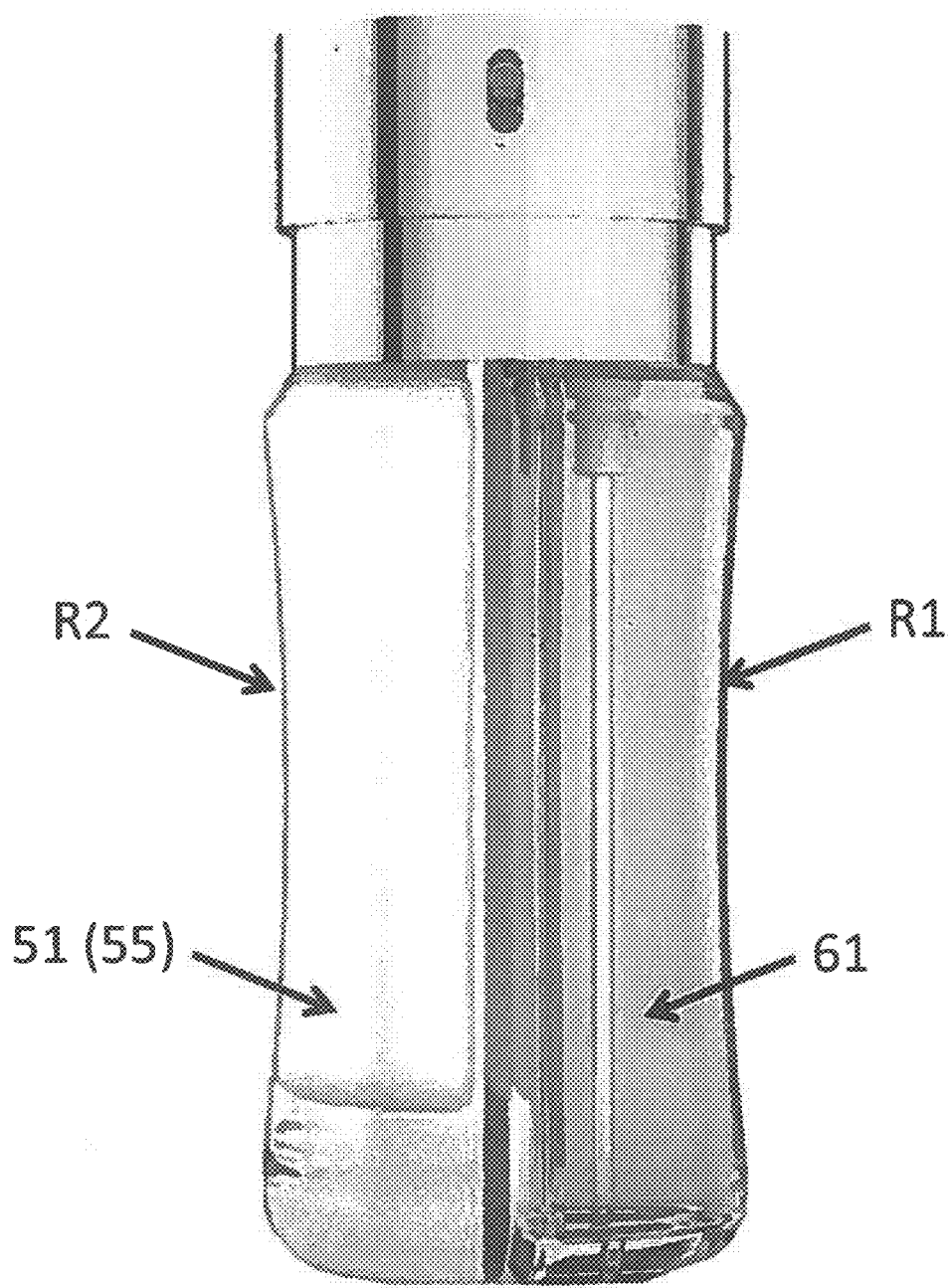
FIG. 6 is a front view of a pair of receptacles containing a first and second composition.

As shown in FIG. 6, the dual dispenser may also contain a first receptacle R1 for storing a first composition 61 and a second receptacle R2 for storing a second composition 51, the second composition containing microcapsules 55. The receptacles R1, R2 may be of any shape or design. In some examples, a shell may not be necessary to house the receptacles; a non-limiting example of which is when the receptacles R1, R2 are made of glass. When the receptacles are made of glass, the two receptacles may be blown from the same piece of molten glass, appearing as a single bottle with two receptacles. Alternatively, when the receptacles are made of glass, the two receptacles may be blown from separate pieces of molten glass, appearing as two bottles, each with a single receptacle, and joined together via a connector. One of ordinary skill in the art will appreciate that many possible designs of the receptacles are possible without deviating from the teachings herein; a non-limiting example of which is a receptacle within a receptacle.

Compositions

Volatile Solvents

The compositions described herein may include a volatile solvent or a mixture of volatile solvents. The volatile solvents may comprise greater than 10%, greater than 30%, greater than 40%, greater than 50%, greater than 60%, greater than 70%, or greater than 90%, by weight of the composition. The volatile solvents useful herein may be relatively odorless and safe for use on human skin. Suitable volatile solvents may include $C_1$-$C_4$ alcohols and mixtures thereof. Some non-limiting examples of volatile solvents include ethanol, methanol, propanol, isopropanol, butanol, and mixtures thereof. In some examples, the composition may comprise from 0.01% to 98%, by weight of the composition, of ethanol.

Nonvolatile Solvents

The composition may comprise a nonvolatile solvent or a mixture of nonvolatile solvents. Non-limiting examples of nonvolatile solvents include benzyl benzoate, diethyl phthalate, isopropyl myristate, propylene glycol, dipropylene glycol, triethyl citrate, and mixtures thereof.

Fragrances

The composition may comprise a fragrance. As used herein, "fragrance" is used to indicate any odoriferous material or a combination of ingredients including at least one odoriferous material. Any fragrance that is cosmetically acceptable may be used in the composition. For example, the fragrance may be one that is a liquid or solid at room temperature. Generally, the non-encapsulated fragrance(s) may be present at a level from about 0.001% to about 40%, from about 0.1% to about 25%, from about 0.25% to about 20%, or from about 0.5% to about 15%, by weight of the composition. Some fragrances can be considered to be volatiles and other fragrances can be considered to be or non-volatiles, as described and defined herein.

A wide variety of chemicals are known as fragrances, non-limiting examples of which include alcohols, aldehydes, ketones, ethers, Schiff bases, nitriles, and esters. More commonly, naturally occurring plant and animal oils and exudates comprising complex mixtures of various chemical components are known for use as fragrances. Non-limiting examples of the fragrances useful herein include pro-fragrances such as acetal pro-fragrances, ketal pro-fragrances, ester pro-fragrances, hydrolyzable inorganic-organic pro-fragrances, and mixtures thereof. The fragrances may be released from the pro-fragrances in a number of ways. For example, the fragrance may be released as a result of simple hydrolysis, or by a shift in an equilibrium reaction, or by a pH-change, or by enzymatic release. The fragrances herein may be relatively simple in their chemical make-up, comprising a single chemical, or may comprise highly sophisticated complex mixtures of natural and synthetic chemical components, all chosen to provide any desired odor.

The fragrances may have a boiling point (BP) of about 500° C. or lower, about 400° C. or lower, or about 350° C. or lower. The BP of many fragrances are disclosed in *Perfume and Flavor Chemicals* (Aroma Chemicals), Steffen Arctander (1969). The C log P value of the individual fragrance materials may be about −0.5 or greater. As used herein, "C log P" means the logarithm to the base 10 of the octanol/water partition coefficient. The C log P can be readily calculated from a program called "C LOG P" which is available from Daylight Chemical Information Systems Inc., Irvine Calif., USA or calculated using Advanced Chemistry Development (ACD/Labs) Software V11.02 (© 1994-2014 ACD/Labs). Octanol/water partition coefficients are described in more detail in U.S. Pat. No. 5,578,563.

Examples of suitable aldehyde include but are not limited to: alpha-Amylcinnamaldehyde, Anisic Aldehyde, Decyl Aldehyde, Lauric aldehyde, Methyl n-Nonyl acetaldehyde, Methyl octyl acetaldehyde, Nonylaldehyde, Benzenecarboxaldehyde, Neral, Geranial, 2, 6 octadiene,1,1 diethoxy-3,7dimethyl-, 4-Isopropylbenzaldehyde, 2,4-Dimethyl-3-cyclohexene-1-carboxaldehyde, alpha-Methyl-p-isopropyldihydrocinnamaldehyde, 3-(3-isopropylphenyl) butanal, alpha-Hexylcinnamaldehyde, 7-Hydroxy-3,7-dimethyloctan-1-al, 2,4-Dimethyl-3-Cyclohexene-1-carboxaldehyde, Octyl Aldehyde, Phenylacetaldehyde, 2,4-Dimethyl-3-Cyclohexene-1-carboxaldehyde, Hexanal, 3,7-Dimethyloctanal, 6,6-Dimethylbicyclo[3.1.1]hept-2-ene-2-butanal, Nonanal, Octanal, 2-Nonenal Undecenal, 2-Methyl-4-(2,6,6-trimethyl-1-cyclohexenyl-1)-2-butenal, 2,6-Dimethyloctanal3-(p-Isopropylphenyl)propionaldehyde, 3-Phenyl-4-pentenal Citronellal, o/p-Ethyl-alpha,alpha-, 9-Decenal, dimethyldihydrocinnamaldehyde, p-Isobutyl-alpha-methyldrocinnamaldehyde, cis-4-Decen-1-al, 2,5-Dimethyl-2-ethenyl-4-hexenal, trans-2-Methyl-2-butenal, 3-Methylnonanal, alpha-Sinensal, 3-Phenylbutanal, 2,2-Dimethyl-3-phenylpropionaldehyde, m-tert.Butyl-alpha-methyldihydrocinnamic aldehyde, Geranyl oxyacetaldehyde, trans-4-Decen-1-al, Methoxycitronellal, and mixtures thereof.

Examples of suitable esters include but are not limited to: Allyl cyclohexanepropionate, Allyl heptanoate, Allyl Amyl Glycolate, Allyl caproate, Amyl acetate (n-Pentyl acetate), Amyl Propionate, Benzyl acetate, Benzyl propionate, Benzyl salicylate, cis-3-Hexenylacetate, Citronellyl acetate, Citronellyl propionate, Cyclohexyl salicylate, Dihydro Isojasmonate Dimethyl benzyl carbinyl acetate, Ethyl acetate, Ethyl acetoacetate, Ethyl Butyrate, Ethyl-2-methyl butryrate, Ethyl-2-methyl pentanoate Fenchyl acetate (1,3, 3-Trimethyl-2-norbornanyl acetate), Tricyclodecenyl acetate, Tricyclodecenyl propionate, Geranyl acetate, cis-3-Hexenyl isobutyrate, Hexyl acetate, cis-3-Hexenyl salicylate, n-Hexyl salicylate, Isobornyl acetate, Linalyl acetate, p-t-Butyl Cyclohexyl acetate, (−)-L-Menthyl acetate, o-t-Butylcyclohexyl acetate), Methyl benzoate, Methyl dihydro iso jasmonate, alpha-Methylbenzyl acetate, Methyl salicylate, 2-Phenylethyl acetate, Prenyl acetate, Cedryl acetate, Cyclabute, Phenethyl phenylacetate, Terpinyl formate, Citronellyl anthranilate, Ethyl tricyclo[5.2.1.0-2,6]decane-2-carboxylate, n-Hexyl ethyl acetoacetate, 2-tert.-Butyl-4-methyl-cyclohexyl acetate, Formic acid, 3,5,5-trimethylhexyl ester, Phenethyl crotonate, Cyclogeranyl acetate, Geranyl crotonate, Ethyl geranate, Geranyl isobutyrate, Ethyl 2-nonynoate2,6-Octadienoic acid, 3,7-dimethyl-, methyl ester, Citronellyl valerate, 2-Hexenylcyclopentanone, Cyclohexyl anthranilate, L-Citronellyl tiglate, Butyl tiglate, Pentyl tiglate, Geranyl caprylate, 9-Decenyl acetate,2-Isopropyl-5-methylhexyl-1 butyrate, n-Pentyl benzoate, 2-Methylbutyl benzoate (mixture with pentyl benzoate), Dimethyl benzyl carbinyl propionate, Dimethyl benzyl carbinyl acetate, trans-2-Hexenyl salicylate, Dimethyl benzyl carbinyl isobutyrate, 3,7-Dimethyloctyl formate, Rhodinyl formate, Rhodinyl isovalerate, Rhodinyl acetate, Rhodinyl butyrate, Rhodinyl propionate, Cyclohexylethyl acetate, Neryl butyrate, Tetrahydrogeranyl butyrate, Myrcenyl acetate, 2,5-Dimethyl-2-ethenylhex-4-enoic acid, methyl ester, 2,4-Dimethylcyclohexane-1-methyl acetate, Ocimenyl acetate, Linalyl isobutyrate, 6-Methyl-5-heptenyl-1 acetate, 4-Methyl-2-pentyl acetate, n-Pentyl 2-methylbutyrate, Propyl acetate, Isopropenyl acetate, Isopropyl acetate, 1-Methylcyclohex-3-enecarboxylic acid, methyl ester, Propyl tiglate, Propyl/isobutyl cyclopent-3-enyl-1-acetate (alpha-vinyl), Butyl 2-furoate, Ethyl 2-pentenoate, (E)-Methyl 3-pentenoate, 3-Methoxy-3-methylbutyl acetate, n-Pentyl crotonate, n-Pentyl isobutyrate, Propyl formate, Furfuryl butyrate, Methyl angelate, Methyl pivalate, Prenyl caproate, Furfuryl propionate, Diethyl malate, Isopropyl 2-methylbutyrate, Dimethyl malonate, Bornyl formate, Styralyl acetate, 1-(2-Furyl)-1-propanone, 1-Citronellyl acetate, 3,7-Dimethyl-1,6-nonadien-3-yl acetate, Neryl crotonate, Dihydromyrcenyl acetate, Tetrahydromyrcenyl acetate, Lavandulyl acetate, 4-Cyclooctenyl isobutyrate, Cyclopentyl isobutyrate, 3-Methyl-3-butenyl acetate, Allyl acetate, Geranyl formate, cis-3-Hexenyl caproate, and mixtures thereof.

Examples of suitable Alcohols include but are not limited to: Benzyl alcohol, beta-gamma-Hexenol (2-Hexen-1-ol), Cedrol, Citronellol, Cinnamic alcohol, p-Cresol, Cumic alcohol, Dihydromyrcenol, 3,7-Dimethyl-1-octanol, Dimethyl benzyl carbinol, Eucalyptol, Eugenol, Fenchyl alcohol, Geraniol, Hydratopic alcohol, Isononyl alcohol (3,5,5-Trimethyl-1-hexanol), Linalool, Methyl Chavicol (Estragole), Methyl Eugenol (Eugenyl methyl ether), Nerol, 2-Octanol, Patchouli alcohol, Phenyl Hexanol (3-Methyl-5-phenyl-1-pentanol), Phenethyl alcohol, alpha-Terpineol, Tetrahydrolinalool, Tetrahydromyrcenol, 4-methyl-3decen-5-ol, 1-3,7-Dimethyloctane-1-ol, 2-(Furfuryl-2)-heptanol, 6,8-Dimethyl-2-nonanol, Ethyl norbornyl cyclohexanol, beta-Methyl cyclohexane ethanol, 3,7-Dimethyl-(2),6-octen (adien)-1-ol, trans-2-Undecen-1-ol 2-Ethyl-2-prenyl-3-hexenol, Isobutyl benzyl carbinol, Dimethyl benzyl carbinol, Ocimenol, 3,7-Dimethyl-1,6-nonadien-3-ol (cis & trans), Tetrahydromyrcenol, alpha-Terpineol, 9-Decenol-1, 2 (Hexenyl)cyclopentanol, 2,6-Dimethyl-2-heptanol, 3-Methyl-1-octen-3-ol, 2,6-Dimethyl-5-hepten-2-ol, 3,7,9-Trimethyl-1,6-decadien-3-ol, 3,7-Dimethyl-6-nonen-1-ol, 3,7-Dimethyl-1-octyn-3-ol, 2,6-Dimethyl-1,5,7-octatrienol-3, Dihydromyrcenol, 2,6,10-Trimethyl-5,9-undecadienol, 2,5-Dimethyl-2-propylhex-4-enol-1,(Z),3-Hexenol, o,m,p-Methyl-phenylethanol, 2-Methyl-5-phenyl-1-pentanol, 3-Methylphenethyl alcohol, para-Methyl dimethyl benzyl carbinol, Methyl benzyl carbinol, p-Methylphenylethanol, 3,7-Dimethyl-2-octen-1-ol, 2-Methyl-6-methylene-7-octen-4-ol, and mixtures thereof.

Examples of ketones include but are not limited to: Oxacycloheptadec-10-en-2-one, Benzylacetone, Benzophenone, L-Carvone, cis-Jasmone, 4-(2,6,6-Trimethyl-3-cyclohexen-1-yl)-but-3-en-4-one, Ethyl amyl ketone, alpha-Ionone, Ionone Beta, Ethanone, Octahydro-2,3,8,8-tetramethyl-2-acetonaphthalene, alpha-Irone, 1-(5,5-Dimethyl-1-cyclohexen-1-yl)-4-penten-1-one, 3-Nonanone, Ethyl hexyl ketone, Menthone, 4-Methylacetophenone, gamma-Methyl Ionone Methyl pentyl ketone, Methyl Heptenone (6-Methyl-5-hepten-2-one), Methyl Heptyl ketone, Methyl Hexyl ketone, delta Muscenone, 2-Octanone, 2-Pentyl-3-methyl-2-cyclopenten-1-one, 2-Heptylcyclopentanone, alpha-Methylionone, 3-Methyl-2-(trans-2-pentenyl)-cyclopentenone, Octenyl cyclopentanone, n-Amylcyclopentenone, 6-Hydroxy-3,7-dimethyloctanoic acid lactone, 2-Hydroxy-2-cyclohexen-1-one, 3-Methyl-4-phenyl-3-buten-2-one, 2-Pentyl-2,5,5-trimethylcyclopentanone, 2-Cyclopentylcyclopentanol-1, 5-Methylhexan-2-one, gamma-Dodecalactone, delta-Dodecalactone delta-Dodecalactone, gamma-Nonalactone, delta-Nonalactone, gamma-Octalactone, delta-Undecalactone, gamma-Undecalactone, and mixtures thereof.

Examples of ethers include but are not limited to: p-Cresyl methyl ether, 4,6,6,7,8,8-Hexamethyl-1,3,4,6,7,8-hexahydro-cyclopenta(G)-2-benzopyran, beta-Naphthyl methyl ether, Methyl Iso Butenyl Tetrahydro Pyran, (Phantolide) 5-Acetyl-1,1,2,3,3,6 hexamethylindan, (Tonalid)7-Acetyl-1,1,3,4,4,6-hexamethyltetralin, 2-Phenylethyl 3-methylbut-2-enyl ether, Ethyl geranyl ether, Phenylethyl isopropyl ether, and mixtures thereof.

Examples of alkenes include but are not limited to: Allo-Ocimene, Camphene, beta-Caryophyllene, Cadinene, Diphenylmethane, d-Limonene, Lymolene, beta-Myrcene, Para-Cymene, alpha-Pinene, beta-Pinene, alpha-Terpinene, gamma-Terpinene, Terpineolene, 7-Methyl-3-methylene-1,6-octadiene, and mixtures thereof.

Examples of nitriles include but are not limited to: 3,7-Dimethyl-6-octenenitrile, 3,7-Dimethyl-2(3), 6-nonadienenitrile, (2E,6Z) 2,6-nonadienenitrile, n-dodecane nitrile, and mixtures thereof.

Examples of Schiffs Bases include but are not limited to: Citronellyl nitrile, Nonanal/methyl anthranilate, Anthranilic acid, N-octylidene-, methyl ester(L)-, Hydroxycitronellal/methyl anthranilate, 2-Methyl-3-(4-Cyclamen aldehyde/methyl anthranilate, methoxyphenyl propanal/Methyl anthranilate, Ethyl p-aminobenzoate/hydroxycitronellal, Citral/methyl anthranilate, 2,4-Dimethylcyclohex-3-enecarbaldehyde methyl anthranilate, Hydroxycitronellal-indole, and mixtures thereof.

Non-limiting examples of fragrances include fragrances such as musk oil, civet, castoreum, ambergris, plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, eucalyptus oil, verbena oil, mimosa extract, narcissus extract, carrot seed extract, jasmine extract, olibanum extract, rose extract, and mixtures thereof.

Carriers and Water

When the composition contains microcapsules, the composition may include a carrier for the microcapsules. Non-limiting examples of carriers include water, silicone oils like silicone D5, and other oils like mineral oil, isopropyl myristate, and fragrance oils. The carrier should be one that does not significantly affect the performance of the microcapsules. Non-limiting examples of non-suitable carriers for the microcapsules include volatile solvents like 95% ethanol.

The compositions containing microcapsules may include about 0.1% to about 95%, from about 5% to about 95%, or from 5% to 75%, by weight of the composition, of the carrier. When the composition contains a volatile solvent, the composition may include from about 0.01% to about 40%, from about 0.1% to about 30%, or from about 0.1% to about 20%, by weight of the composition, of water.

In some examples, when a first composition containing a volatile solvent and a second composition containing microcapsules are sprayed, the dose containing the mixture of the first and second compositions may contain about 0.01% to about 75%, from about 1% to about 60%, from about 0.01% to about 60%, or from about 5% to about 50%, by weight of the composition, of water.

Encapsulates

The microcapsules may be any kind of microcapsule disclosed herein or known in the art. The microcapsules may be included from about 0.01% to about 45%, by weight, of the composition. The microcapsules may have a shell and a core material encapsulated by the shell. The core material of the microcapsules may include one or more perfume oils. The shells of the microcapsules may be made from synthetic polymeric materials or naturally-occurring polymers. Synthetic polymers may be derived from petroleum oil, for example. Non-limiting examples of synthetic polymers include nylon, polyethylenes, polyamides, polystyrenes, polyisoprenes, polycarbonates, polyesters, polyureas, polyurethanes, polyolefins, polysaccharides, epoxy resins, vinyl polymers, polyacrylates, and mixtures thereof. Natural polymers occur in nature and may often be extracted from natural materials. Non-limiting examples of naturally occurring polymers are silk, wool, gelatin, cellulose, proteins, and combinations thereof.

The microcapsules may be friable microcapsules. A friable microcapsule is configured to release its core material when its shell is ruptured. The rupture may be caused by forces applied to the shell during mechanical interactions. The microcapsules may have a shell with a volume weighted fracture strength of from about 0.1 mega Pascals to about 15.0 mega Pascals, when measured according to the Fracture Strength Test Method described herein, or any incremental value expressed in 0.1 mega Pascals in this range, or any range formed by any of these values for fracture strength. As an example, a microcapsule may have a shell with a volume weighted fracture strength of 0.8-15.0 mega Pascals (MPa), alternatively from 5.0-12.0 mega Pascals (MPa), or alternatively from 6.0-10.0 mega Pascals (MPa).

The microcapsules may have a median volume-weighted particle size of from 2 microns to 80 microns, from 10 microns to 30 microns, or from 10 microns to 20 microns, as determined by the Test Method for Determining Median Volume-Weighted Particle Size of Microcapsules described herein.

The microcapsules may have various core material to shell weight ratios. The microcapsules may have a core material to shell ratio that is greater than or equal to: 70% to 30%, 75% to 25%, 80% to 20%, 85% to 15%, 90% to 10%, and 95% to 5%.

The microcapsules may have shells made from any material in any size, shape, and configuration known in the art. Some or all of the shells may include a polyacrylate material, such as a polyacrylate random copolymer. For example, the polyacrylate random copolymer may have a total polyacrylate mass, which includes ingredients selected from the group including: amine content of 0.2-2.0% of total polyacrylate mass; carboxylic acid of 0.6-6.0% of total polyacrylate mass; and a combination of amine content of 0.1-1.0% and carboxylic acid of 0.3-3.0% of total polyacrylate mass.

When a microcapsule's shell includes a polyacrylate material, and the shell has an overall mass, the polyacrylate material may form 5-100% of the overall mass, or any integer value for percentage in this range, or any range formed by any of these values for percentage. As examples, the polyacrylate material may form at least 5%, at least 10%, at least 25%, at least 33%, at least 50%, at least 70%, or at least 90% of the overall mass.

Some or all of the microcapsules may have various shell thicknesses. For at least a first group of the provided microcapsules, each microcapsule may have a shell with an overall thickness of 1-300 nanometers, or any integer value for nanometers in this range, or any range formed by any of these values for thickness. As an example, microcapsules may have a shell with an overall thickness of 2-200 nanometers.

The microcapsules may also encapsulate one or more benefit agents. The benefit agent(s) include, but are not limited to, cooling sensates, warming sensates, perfume oils, oils, pigments, dyes, chromogens, phase change materials, and other kinds of benefit agent known in the art, in any combination. In some examples, the perfume oil encapsulated may have a C log P of less than 4.5 or a C log P of less than 4. Alternatively the perfume oil encapsulated may have a C log P of less than 3. In some examples, the microcapsule may be anionic, cationic, zwitterionic, or have a neutral charge. The benefit agents(s) may be in the form of solids and/or liquids. The benefit agent(s) may be any kind of perfume oil(s) known in the art, in any combination.

The microcapsules may encapsulate a partitioning modifier in addition to the benefit agent. Non-limiting examples of partitioning modifiers include isopropyl myristate, mono-, di-, and tri-esters of $C_4$-$C_{24}$ fatty acids, castor oil, mineral oil, soybean oil, hexadecanoic acid, methyl ester isododecane, isoparaffin oil, polydimethylsiloxane, brominated vegetable oil, and combinations thereof. Microcapsules may also have varying ratios of the partitioning modifier to the benefit agent so as to make different populations of microcapsules that may have different bloom patterns. Such populations may also incorporate different perfume oils so as to make populations of microcapsules that display different bloom patterns and different scent experiences. U.S. 2011-0268802 discloses other non-limiting examples of microcapsules and partitioning modifiers and is hereby incorporated by reference.

The microcapsule's shell may comprise a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator. In some examples, said amine is an aminoalkyl acrylate or aminoalkyl methacrylate.

The microcapsules may include a core material and a shell surrounding the core material, wherein the shell comprises: a plurality of amine monomers selected from the group consisting of aminoalkyl acrylates, alkyl aminoalkyl acrylates, dialkyl aminoalykl acrylates, aminoalkyl methacrylates, alkylamino aminoalkyl methacrylates, dialkyl aminoalykl methacrylates, tertiarybutyl aminethyl methacrylates, diethylaminoethyl methacrylates, dimethylaminoethyl methacrylates, dipropylaminoethyl methacrylates, and mixtures thereof; and a plurality of multifunctional monomers or multifunctional oligomers. Non-limiting examples of emulsifiers include water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates, palmitamidopropyltrimonium chloride (Varisoft PATC™, available from Degussa Evonik, Essen, Germany), distearyl dimonium chloride, cetyltrimethylammonium chloride, quaternary ammonium compounds, fatty amines, aliphatic ammonium halides, alkyldimethylbenzylammonium halides, alkyldimethylethylammonium halides, polyethyleneimine, poly(2-dimethylamino)ethyl methacrylate) methyl chloride quaternary salt, poly(1-vinylpyrrolidone-co-2-dimethylaminoethyl methacrylate), poly(acrylamide-co-diallyldimethylammonium chloride), poly(allylamine), poly[bis(2-chloroethyl) ether-alt-1,3-bis[3-(dimethylamino)propyl]urea] quaternized, and poly(dimethylamine-co-epichlorohydrin-co-ethylenediamine), condensation products of aliphatic amines with alkylene oxide, quaternary ammonium compounds with a long-chain aliphatic radical, e.g. distearyldiammonium chloride, and fatty amines, alkyldimethylbenzylammonium halides, alkyldimethylethylammonium halides, polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, polyvinyl acetate, or copolymers of polyvinyl alcohol polyvinyl acetate, polyacrylamide, poly(N-isopropylacrylamide), poly(2-hydroxypropyl methacrylate), poly(2-ethyl-2-oxazoline), poly(2-isopropenyl-2-oxazoline-co-methyl methacrylate), poly(methyl vinyl ether), and polyvinyl alcohol-co-ethylene), and cocoamidopropyl betaine.

Processes for making microcapsules are well known. Various processes for microencapsulation, and exemplary methods and materials, are set forth in U.S. Pat. No. 6,592,990; U.S. Pat. No. 2,730,456; U.S. Pat. No. 2,800,457; U.S. Pat. No. 2,800,458; U.S. Pat. No. 4,552,811; and U.S. 2006/0263518 A1.

The microcapsule may be spray-dried to form spray-dried microcapsules. The composition may also contain one or more additional delivery systems for providing one or more benefit agents, in addition to the microcapsules. The additional delivery system(s) may differ in kind from the microcapsules. For example, wherein the microcapsule encapsulates a perfume oil, the additional delivery system may be an additional fragrance delivery system, such as a moisture-triggered fragrance delivery system. Non-limiting examples of moisture-triggered fragrance delivery systems include cyclic oligosaccharide, starch (or other polysaccharide material), starch derivatives, and combinations thereof. Said polysaccharide material may or may not be modified.

The plurality of microcapsules may include anionic, cationic, and non-ionic microcapsules, in any combination, when included in a composition with a pH range of from 2 to about 10, alternatively from about 3 to about 9, alternatively from about 4 to about 8.

In some examples, the microcapsules may include a benefit agent comprising: a.) a perfume composition having a C log P of less than 4.5; b.) a perfume composition comprising, based on total perfume composition weight, 60% perfume materials having a C log P of less than 4.0; c.) a perfume composition comprising, based on total perfume composition weight, 35% perfume materials having a C log P of less than 3.5; d.) a perfume composition comprising, based on total perfume composition weight, 40% perfume materials having a C log P of less than 4.0 and at least 1% perfume materials having a C log P of less than 2.0; e.) a perfume composition comprising, based on total perfume composition weight, 40% perfume materials having a C log P of less than 4.0 and at least 15% perfume materials having a C log P of less than 3.0; f.) a perfume composition comprising, based on total perfume composition weight, at least 1% butanoate esters and at least 1% of pentanoate esters; g.) a perfume composition comprising, based on total perfume composition weight, at least 2% of an ester comprising an allyl moiety and at least 10% of another perfume comprising an ester moiety; h.) a perfume composition comprising, based on total perfume composition weight, at least 1% of an aldehyde comprising an alkyl chain moiety; i.) a perfume composition comprising, based on total perfume composition weight, at least 2% of a butanoate ester; j.) a perfume composition comprising, based on total perfume composition weight, at least 1% of a pentanoate ester; k.) a perfume composition comprising, based on total perfume composition weight, at least 3% of an ester comprising an allyl moiety and 1% of an aldehyde comprising an alkyl chain moiety; l.) a perfume composition comprising, based on total perfume composition weight, at least 25% of a perfume comprising an ester moiety and 1% of an aldehyde comprising an alkyl chain moiety; m.) a perfume composition comprising, based on total perfume composition weight, at least 2% of a material selected from 4-(2,6,6-trimethyl-1-cyclohexenyl)-3-buten-2-one, 4-(2,6,6-trimethyl-2-cyclohexenyl)-3-buten-2-one and 3-buten-2-one, 3-methyl-4-(2,6,6-trimehtyl-1-cyclohexen-2-yl)- and mixtures thereof; n.) a perfume composition comprising, based on total perfume composition weight, at least 0.1% of tridec-2-enonitrile, and mandaril, and mixtures thereof; o.) a perfume composition comprising, based on total perfume composition weight, at least 2% of a material selected from 3,7-dimethyl-6-octene nitrile, 2-cyclohexylidene-2-phenylacetonitrile and mixtures thereof; p.) a perfume composition comprising, based on total perfume composition weight, at least 80% of one or more perfumes comprising a moiety selected from the group consisting of esters, aldehydes, ionones, nitriles, ketones and combinations thereof; q.) a perfume composition comprising, based on total perfume composition weight, at least 3% of an ester comprising an allyl moiety; a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhexyl-4-enyl acetate; p-metnh-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid, 3-(1-methylethyl)-ethyl ester; bycyclo [2.2.1]heptan-2-ol, 1,7,7-trimethyl-, acetate; 1,5-dimethyl-1-ethenylhex-4-enylacetate; hexyl 2-methyl propanoate; ethyl-2-methylbutanoate; 4-undecanone; 5-heptyldihydro-2(3h)-furanone; 1,6-nonadien-3-ol, 3,7dimethyl-; 3,7-dimethylocta-1,6-dien-3-o; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; hexyl ethanoate, 7-acetyl, 1,2,3,4,5,6,7,8-octahydro-1,1,6,7-tetramethyl naphtalene; allyl-cyclohexyloxy acetate; methyl nonyl acetic aldehyde; 1-spiro[4,5]dec-7-en-7-yl-4-pentenen-1-one; 7-octen-2-ol, 2-methyl-6-methylene-,dihydro; cyclohexanol, 2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one, 3-methyl-4-(2,6,6-trimethyl-1-cyclohexen-2-yl)-; hexanoic acid, 2-propenyl ester; (z)-non-6-en-1-al; 1-decyl aldehyde; 1-octanal; 4-t-butyl- -methylhydrocinnamaldehyde; alpha-hexylcinnamaldehyde; ethyl-2,4-hexadienoate; 2-propenyl 3-cyclohexanepropanoate; and mixtures thereof; r.) a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhex-4-enyl acetate; p-menth-1-en-8-yl acetate; 4-(2,6,6-trimethyl-2-cyclohexenyl)-3-buten-2-one; 4-acetoxy-3-methoxy-1- propenylbenzene; 2-propenyl cyclohexanepropionate; bicyclo[2.2.1]hept-5-ene-2-carboxylic acid, 3-(1-methylethyl)-ethyl ester; bycyclo [2.2.1]heptan-2-ol, 1,7,7-trimethyl-, acetate; 1,5-dimethyl-1-ethenylhex-4-enyl acetate; hexyl 2-methyl propanoate; ethyl-2-methylbutanoate,4-undecanolide; 5-heptyldihydro-2(3h)-furanone; 5-hydroxydodecanoic acid; decalactones; undecalactones, 1,6-nonadien-3-ol, 3,7dimethyl-; 3,7-dimethylocta-1,6-dien-3-ol; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; allyl-cyclohexyloxy acetate; methyl nonyl acetic aldehyde; 1-spiro[4,5]dec-7-en-7-yl-4-pentenen-1-one; 7-octen-2-ol, 2-methyl-6-methylene-,dihydro, cyclohexanol, 2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one, 3-methyl-4-(2,6,6-trimehtyl-1-cyclohexen-2-yl)-; hexanoic acid, 2-propenyl ester; (z)-non-6-en-1-al; 1-decyl aldehyde; 1-octanal; 4-t-butyl--methylhydrocinnamaldehyde; ethyl-2,4-hexadienoate; 2-propenyl 3-cyclohexanepropanoate; and mixtures thereof; s.) a perfume composition comprising, based on total perfume composition weight, at least 5% of a material selected from the group consisting of 3-cyclohexene-1-carboxaldehyde,dimethyl-; 3-buten-2-one, 3-methyl-4-(2,6,6-trimethyl-1-cyclohexen-2-yl)-; patchouli oil; Hexanoic acid, 2-propenyl ester; 1-Octanal; 1-decyl aldehyde; (z)-non-6-en-1-al; methyl nonyl acetic aldehyde; ethyl-2-methylbutanoate; 1-methylethyl-2-methylbutanoate; ethyl-2-methyl pentanoate; 4-hydroxy-3-ethoxybenzaldehyde; 4-hydroxy-3-methoxybenzaldehyde; 3-hydroxy-2-methyl-4-pyrone; 3-hydroxy-2-ethyl-4-pyrone and mixtures thereof; t.) a perfume composition comprising, based on total perfume composition weight, less than 10% perfumes having a C log P greater than 5.0; u.) a perfume composition comprising geranyl palmitate; or v.) a perfume composition comprising a first and an optional second material, said first material having: (i) a C log P of at least 2; (ii) a boiling point of less than about 280° C.; and second optional second material, when present, having (i) a C log P of less than 2.5; and (ii) a ODT of less than about 100 ppb.

In some examples, the microcapsules may include a benefit agent comprising: one or more materials selected from the group consisting of (5-methyl-2-propan-2-ylcyclohexyl) acetate; 3,7-dimethyloct-6-en-1-al; 2-(phenoxy)ethyl 2-methylpropanoate; prop-2-enyl 2-(3-methylbutoxy)acetate; 3-methyl-1-isobutylbutyl acetate; prop-2-enyl hexanoate; prop-2-enyl 3-cyclohexylpropanoate; prop-2-enyl heptanoate; (E)-1-(2,6,6-trimethyl-1-cyclohex-2-enyl)but-2-en-1-one; (E)-4-(2,6,6-trimethyl-1-cyclohex-2-enyl)but-3-en-2-one; (E)-3-methyl-4-(2,6,6-trimethyl-1-cyclohex-2-enyl)but-3-en-2-one; 1-(2,6,6-trimethyl-1-cyclohex-2-enyl)pent-1-en-3-one; 6,6,9a-trimethyl-1,2,3a,4,5,5a,7,8,9,9b-decahydronaphtho[2,1-b]furan; pentyl 2-hydroxybenzoate; 7,7-dimethyl-2-methylidene-norbornane; (E)-1-(2,6,6-trimethyl-1-cyclohexenyl)but-2-en-1-one; (E)-4-(2,6,6-trimethyl-1-cyclohexenyl)but-3-en-2-one; 4-ethoxy-4,8,8-trimethyl-9-methylidenebicyclo[3.3.1] nonane; (1,7,7-trimethyl-6-bicyclo[2.2.1]heptanyl) acetate; 3-(4-tert-butylphenyl)propanal; 1,1,2,3,3-pentamethyl-2,5,6,7-tetrahydroinden-4-one; 2-oxabicyclo2.2.2octane, 1methyl4(2,2,3trimethylcyclopentyl); [(Z)-hex-3-enyl] acetate; [(Z)-hex-3-enyl] 2-methylbutanoate; cis-3-hexenyl 2-hydroxybenzoate; 3,7-dimethylocta-2,6-dienal; 3,7-dimethyloct-6-en-1-al; 3,7-dimethyl-6-octen-1-ol; 3,7-dimethyloct-6-enyl acetate; 3,7-dimethyloct-6-enenitrile; 2-(3,7-dimethyloct-6-enoxy)acetaldehyde; tetrahydro-4-methyl-2-propyl-2h-pyran-4-yl acetate; ethyl 3-phenyloxirane-2-carboxylate; hexahydro-4,7-methano-indenyl isobutyrate; 2,4-dimethylcyclohex-3-ene-1-carbaldehyde; hexahydro-4,7-methano-indenyl propionate; 2-cyclohexylethyl acetate; 2-pentylcyclopentan-1-ol; (2R,3R,4S,5S,6R)-2-[(2R,3S,4R,5R,6R)-6-(6-cyclohexylhexoxy)-4,5-dihydroxy-2-(hydroxymethyl)oxan-3-yl]oxy-6-(hydroxymethyl)oxane-3,4,5-triol; (E)-1-(2,6,6-trimethyl-1-cyclohexa-1,3-dienyl)but-2-en-1-one; 1-cyclohexylethyl (E)-but-2-enoate; dodecanal; (E)-1-(2,6,6-trimethyl-1-cyclohex-3-enyl)but-2-en-1-one; (5E)-3-methylcyclopentadec-5-en-1-one; 4-(2,6,6-trimethyl-1-cyclohex-2-enyl)butan-2-one; 2-methoxy-4-propylphenol; methyl 2-hexyl-3-oxocyclopentane-1-carboxylate; 2,6-dimethyloct-7-en-2-ol; 4,7-dimethyloct-6-en-3-one; 4-(octahydro-4,7-methano-5H-inden-5-yliden)butanal; acetaldehyde ethyl linalyl acetal; ethyl 3,7-dimethyl-2,6-octadienoate; ethyl 2,6,6-trimethylcyclohexa-1,3-diene-1-carboxylate; 2-ethylhexanoate; (6E)-3,7-dimethylnona-1,6-dien-3-ol; ethyl 2-methylbutanoate; ethyl 2-methylpentanoate; ethyl tetradecanoate; ethyl nonanoate; ethyl 3-phenyloxirane-2-carboxylate; 1,4-dioxacycloheptadecane-5,17-dione; 1,3,3-trimethyl-2-oxabicyclo[2,2,2]octane; [essential oil]; oxacyclo-hexadecan-2-one; 3-(4-ethylphenyl)-2,2-dimethylpropanal; 2-butan-2-ylcyclohexan-1-one; 1,4-cyclohexandicarboxylic acid, diethyl ester; (3aalpha,4beta,7beta,7aalpha)-octahydro-4,7-methano-3aH-indene-3a-carboxylic acid ethyl ester; hexahydro-4-7, menthano-1H-inden-6-yl propionate; 2-butenon-1-one, 1-(2,6-dimethyl-6-methylencyclohexyl)-; (E)-4-(2,2-dimethyl-6-methylidenecyclohexyl)but-3-en-2-one; 1-methyl-4-propan-2-ylcyclohexa-1,4-diene; 5-heptyloxolan-2-one; 3,7-dimethylocta-2,6-dien-1-ol; [(2E)-3,7-dimethylocta-2,6-dienyl] acetate; [(2E)-3,7-dimethylocta-2,6-dienyl] octanoate; ethyl 2-ethyl-6,6-dimethylcyclohex-2-ene-1-carboxylate; (4-methyl-1-propan-2-yl-1-cyclohex-2-enyl) acetate; 2-butyl-4,6-dimethyl-5,6-dihydro-2H-pyran; oxacyclohexadecen-2-one; 1-propanol, 2-[1-(3,3-dimethyl-cyclohexyl)ethoxy]-2-methyl-propanoate; 1-heptyl acetate; 1-hexyl acetate; hexyl 2-methylpropanoate; (2-(1-ethoxyethoxy)ethyl)benzene; 4,4a,5,9b-tetrahydroindeno[1,2-d][1,3]dioxine; undec-10-enal; 3-methyl-4-(2,6,6-trimethyl-2-cyclohexen-1-yl)-3-buten-2-one; 1-(1,2,3,4,5,6,7,8-octahydro-2,3,8,8-tetramethyl-2-naphthalenyl)-ethan-1-one; 7-acetyl, 1,2,3,4,5,6,7-octahydro-1,1,6,7,-tetra methyl naphthalene; 3-methylbutyl 2-hydroxybenzoate; [(1R,4S,6R)-1,7,7-trimethyl-6-bicyclo[2.2.1]heptanyl] acetate; [(1R,4R,6R)-1,7,7-trimethyl-6-bicyclo[2.2.1]heptanyl] 2-methylpropanoate; (1,7,7-trimethyl-5-bicyclo[2.2.1]heptanyl) propanoate; 2-methylpropyl hexanoate; [2-methoxy-4-[(E)-prop-1-enyl]phenyl] acetate; 2-hexylcyclopent-2-en-1-one; 5-methyl-2-propan-2-ylcyclohexan-1-one; 7-methyloctyl acetate; propan-2-yl 2-methylbutanoate; 3,4,5,6,6-pentamethylheptenone-2; hexahydro-3,6-dimethyl-2(3H)-benzofuranone; 2,4,4,7-tetramethyl-6,8-nonadiene-3-one oxime; dodecyl acetate; [essential oil]; 3,7-dimethylnona-2,6-dienenitrile; [(Z)-hex-3-enyl] methyl carbonate; 2-methyl-3-(4-tert-butylphenyl)propanal; 3,7-dimethylocta-1,6-dien-3-ol; 3,7-dimethylocta-1,6-dien-3-yl acetate; 3,7-dimethylocta-1,6-dien-3-yl butanoate; 3,7-dimethylocta-1,6-dien-3-yl formate; 3,7-dimethylocta-1,6-dien-3-yl 2-methylpropanoate; 3,7-dimethylocta-1,6-dien-3-yl propanoate; 3-methyl-7-propan-2-ylbicyclo[2.2.2]oct-2-ene-5-carbaldehyde; 2,2-dimethyl-3-(3-methylphenyl)propan-1- ol; 3-(4-tert-butylphenyl)butanal; 2,6-dimethylhept-5-enal; 5-methyl-2-propan-2-yl-cyclohexan-1-ol; 1-(2,6,6-trimethyl-1-cyclohexenyl)pent-1-en-3-one; methyl 3-oxo-2-pentylcyclopentaneacetate; methyl tetradecanoate; 2-methylundecanal; 2-methyldecanal; 1,1-dimethoxy-2,2,5-trimethyl-4-hexene; [(1S)-3-(4-methylpent-3-enyl)-1-cyclohex-3-enyl]methyl acetate; 2-(2-(4-methyl-3-cyclohexen-1-yl) propyl)cyclo-pentanone; 4-penten-1-one, 1-(5,5-dimethyl-1-cyclohexen-1-yl; 1H-indene-ar-propanal,2,3,-dihydro-1, 1-dimethyl-(9CI); 2-ethoxynaphthalene; nonanal; 2-(7,7-dimethyl-4-bicyclo[3.1.1]hept-3-enyl)ethyl acetate; octanal; 4-(1-methoxy-1-methylethyl)-1-methylcyclohexene; (2-tert-butylcyclohexyl) acetate; (E)-1-ethoxy-4-(2-methylbutan-2-yl)cyclohexane; 1,1-dimethoxynon-2-yne; [essential oil]; 2-cyclohexylidene-2-phenylacetonitrile; 2-cyclohexyl-1,6-heptadien-3-one; 4-cyclohexyl-2-methylbutan-2-ol; 2-phenylethyl 2-phenylacetate; (2E,5E/Z)-5,6,7-trimethyl octa-2,5-dien-4-one; 1-methyl-3-(4-methylpent-3-enyl)cyclohex-3-ene-1-carbaldehyde; methyl 2,2-dimethyl-6-methylidenecyclohexane-1-carboxylate; 1-(3,3-dimethylcyclohexyl)ethyl acetate; 4-methyl-2-(2-methylprop-1-enyl)oxane; 1-spiro(4.5)-7-decen-7-yl-4-penten-1-one; 4-(2-butenylidene)-3,5,5-trimethylcyclohex-2-en-1-one; 2-(4-methyl-1-cyclohex-3-enyl)propan-2-ol; 4-isopropylidene-1-methyl-cyclohexene; 2-(4-methyl-1-cyclohex-3-enyl)propan-2-yl acetate; 3,7-dimethyloctan-3-ol; 3,7-dimethyloctan-3-ol; 3,7-dimethyloctan-3-yl acetate; 3-phenylbutanal; (2,5-dimethyl-4-oxofuran-3-yl) acetate; 4-methyl-3-decen-5-ol; undec-10-enal; (4-formyl-2-methoxyphenyl) 2-methylpropanoate; 2,2,5-trimethyl-5-pentylcyclopentan-1-one; 2-tert-butylcyclohexan-1-ol; (2-tert-butylcyclohexyl) acetate; 4-tert-butylcyclohexyl acetate; 1-(3-methyl-7-propan-2-yl-6-bicyclo[2.2.2] oct-3-enyl)ethanone; (4,8-dimethyl-2-propan-2-ylidene-3,3a,4,5, 6,8a-hexahydro-1H-azulen-6-yl) acetate; [(4Z)-1-cyclooct-4-enyl] methyl carbonate; methyl beta naphtyl ether; materials and stereoisomers thereof.

The compositions may also include a parent fragrance and one or more encapsulated fragrances that may or may not differ from the parent fragrance. For example, the composition may include a parent fragrance and a non-parent fragrance. A parent fragrance refers to a fragrance that is dispersed throughout the composition and is typically not encapsulated when added to the composition. Herein, a non-parent fragrance refers to a fragrance that differs from a parent fragrance included within the composition and is encapsulated with an encapsulating material prior to inclusion into the composition. Non-limiting examples of differences between a fragrance and a non-parent fragrance include differences in chemical make-up. In some examples, dried microcapsules may be incorporated into the composition, prepared by spray drying, fluid bed drying, tray drying, or other such drying processes that are available.

Suspending Agents

The compositions described herein may include one or more suspending agents to suspend the microcapsules and other water-insoluble material dispersed in the composition. The concentration of the suspending agent may range from about 0.01% to about 90%, alternatively from about 0.01% to 15% by weight of the composition.

Non-limiting examples of suspending agents include anionic polymers, cationic polymers, and nonionic polymers. Non-limiting examples of said polymers include vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (Cydonia oblonga Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate and alginic acid, propylene glycol esters, acrylate polymers such as sodium polyacrylate, polyethylacrylate, polyacrylamide, and polyethyleneimine, and inorganic water soluble material such as bentonite, aluminum magnesium silicate, laponite, hectonite, and anhydrous silicic acid. Other suspending agents may include, but are not limited to, Konjac, Gellan, and a methyl vinyl ether/maleic anhydride copolymer crosslinked with decadiene (e.g. Stabileze®).

Other non-limiting examples of suspending agents include cross-linked polyacrylate polymers like Carbomers with the trade names Carbopol® 934, Carbopol® 940, Carbopol® 950, Carbopol® 980, Carbopol® 981, Carbopol® Ultrez 10, Carbopol® Ultrez 20, Carbopol® Ultrez 21, Carbopol® Ultrez 30, Carbopol® ETD2020, Carbopol® ETD2050, Pemulen® TR-1, and Pemulen® TR-2, available from The Lubrizol Corporation; acrylates/steareth-20 methacrylate copolymer with trade name ACRYSOL™ 22 available from Rohm and Hass; acrylates/beheneth-25 methacrylate copolymers, trade names including Aculyn-28 available from Rohm and Hass, and Volarest™ FL available from Croda; nonoxynyl hydroxyethylcellulose with the trade name Amercell™ POLYMER HM-1500 available from Amerchol; methylcellulose with the trade name BENECEL®, hydroxyethyl cellulose with the trade name NATROSOL®; hydroxypropyl cellulose with the trade name KLUCEL®; cetyl hydroxyethyl cellulose with the trade name POLYSURF® 67, supplied by Hercules; ethylene oxide and/or propylene oxide based polymers with the trade names CARBOWAX® PEGs, POLYOX WASRs, and UCON® FLUIDS, all supplied by Amerchol; ammonium acryloyl dimethyltaurate/carboxyethyl-acrylate-crosspolymers like Aristoflex® TAC copolymer, ammonium acryloyl dimethyltaurate/VP copolymers like Aristoflex® AVS copolymer, sodium acryloyl dimethyltaurate/VP crosspolymers like Aristoflex® AVS copolymer, ammonium acryloyl dimethyltaurate/beheneth-25 methacrylate crosspolymers like Aristoflex® BVL or HMB, all available from Clariant Corporation; polyacrylate crosspoylmer-6 with the trade name Sepimax™ Zen, available from Seppic; and crosslinked copolymers of vinyl pyrrolidone and acrylic acid such as UltraThix™ P-100 polymer available from Ashland.

Other non-limiting examples of suspending agents include crystalline suspending agents which can be categorized as acyl derivatives, long chain amine oxides, and mixtures thereof.

Other non-limiting examples of suspending agents include ethylene glycol esters of fatty acids, in some aspects those having from about 16 to about 22 carbon atoms; ethylene glycol stearates, both mono and distearate, in some aspects, the distearate containing less than about 7% of the mono stearate; alkanol amides of fatty acids, having from about 16 to about 22 carbon atoms, or about 16 to 18 carbon atoms, examples of which include stearic monoethanolamide, stearic diethanolamide, stearic monoisopropanolamide and stearic monoethanolamide stearate; long chain acyl derivatives including long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin), a commercial example of which is Thixin® R available from Rheox, Inc. Other non-limiting examples of suspending agents include long chain acyl derivatives, ethylene glycol esters of long chain carboxylic acids, long chain amine oxides, and alkanol amides of long chain carboxylic acids.

Other non-limiting examples of suspending agents include long chain acyl derivatives including N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Non-limiting examples of suitable long chain amine oxides for use as suspending agents include alkyl dimethyl amine oxides (e.g., stearyl dimethyl amine oxide).

Other non-limiting suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Other non-limiting examples of suspending agents include di(hydrogenated tallow) phthalic acid amide, and cross-linked maleic anhydride-methyl vinyl ether copolymer.

Coloring Agents

The compositions herein may include a coloring agent. A coloring agent may be in the form of a pigment. As used herein, the term "pigment" means a solid that reflects light of certain wavelengths while absorbing light of other wavelengths, without providing appreciable luminescence. Useful pigments include, but are not limited to, those which are extended onto inert mineral(s) (e.g., talk, calcium carbonate, clay) or treated with silicone or other coatings (e.g., to prevent pigment particles from re-agglomerating or to change the polarity (hydrophobicity) of the pigment. Pigments may be used to impart opacity and color. Any pigment that is generally recognized as safe (such as those listed in C.T.F.A. cosmetic Ingredient Handbook, $3^{rd}$ Ed., cosmetic and Fragrance Association, Inc., Washington, D.C. (1982), herein incorporated by reference) may be included in the compositions described herein. Non-limiting examples of pigments include body pigment, inorganic white pigment, inorganic colored pigment, pearling agent, and the like. Non-limiting examples of pigments include talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, polyethylene powder, methacrylate powder, polystyrene powder, silk powder, crystalline cellulose, starch, titanated mica, iron oxide titanated mica, bismuth oxychloride, and the like. The aforementioned pigments can be used independently or in combination.

Other non-limiting examples of pigments include inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. Non-limiting examples of pigments include nanocolorants from BASF and multi-layer interference pigments such as Sicopearls from BASF. The pigments may be surface treated to provide added stability of color and ease of formulation. Non-limiting examples of pigments include aluminum, barium or calcium salts or lakes. Some other non-limiting examples of coloring agents include Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake.

A coloring agent may also be a dye. Non-limiting examples include Red 6, Red 21, Brown, Russet and Sienna dyes, Yellow 5, Yellow 6, Red 33, Red 4, Blue 1, Violet 2, and mixtures thereof. Other non-limiting examples of dyes include fluorescent dyes like fluorescein.

Other Ingredients

The compositions may include other ingredients like antioxidants, ultraviolet inhibitors like sunscreen agents and physical sunblocks, cyclodextrins, quenchers, and/or skin care actives. Non-limiting examples of other ingredients include 2-ethylhexyl-p-methoxycinnamate; hexyl 2-[4-(diethylamino)-2-hydroxybenzoyl]benzoate; 4-tert-butyl-4'-methoxy dibenzoylmethane; 2-hydroxy-4-methoxybenzophenone; 2-phenylbenzimidazole-5-sulfonic acid; octocrylene; zinc oxide; titanium dioxide; vitamins like vitamin C, vitamin B, vitamin A, vitamin E, and derivatives thereof; flavones and flavonoids; amino acids like glycine, tyrosine, etc.; carotenoids and carotenes; chelating agents like EDTA, lactates, citrates, and derivatives thereof.

First and Second Compositions

The dispenser may include a first composition stored in a first receptacle and a second composition stored in the second receptacle. The first composition may include a volatile solvent and a first fragrance. The second composition may include a plurality of microcapsules and a carrier (e.g. water). The second composition my further include a suspending agent. The first and second compositions may each further include any other ingredient listed herein unless such an ingredient negatively affects the performance of the microcapsules. Non-limiting examples of other ingredients include a coloring agent included in at least one of the first and second compositions and at least one non-encapsulated fragrance in the first composition or second composition. When the second composition comprises microcapsules encapsulating a fragrance, the second compositions may further include a non-encapsulated fragrance that may or may not differ from the encapsulated fragrance in chemical make-up. In some examples, the second composition may be substantially free of a material selected from the group consisting of a propellant, ethanol, a detersive surfactant, and combinations thereof; preferably free of a material selected from the group consisting of a propellant, ethanol, a detersive surfactant, and combinations thereof. Non-limiting examples of propellants include compressed air, nitrogen, inert gases, carbon dioxide, gaseous hydrocarbons like propane, n-butane, isobutene, cyclopropane, and mixtures thereof. In some examples, the first composition may be substantially free of a material selected from the group consisting of a propellant, microcapsules, a detersive surfactant, and combinations thereof; preferably free of a material selected from the group consisting of propellant, microcapsules, a detersive surfactant, and combinations thereof. At least some of the microcapsules included in such a dispenser may encapsulate a fragrance. The fragrance encapsulated within the microcapsules may or may not differ in chemical make-up from the non-encapsulated fragrance included with the volatile solvent.

In some examples, the second composition may include at least 50%, at least 75%, or even at least 90%, by weight of the composition, of water; a plurality of microcapsules; and from about 0.01% to about 90%, preferably from about 0.01% to about 15%, more preferably from about 0.5% to about 15%, by weight of the composition, of a suspending agent; wherein the composition is free of propellants, volatile solvents (e.g. ethanol), and detersive surfactants; wherein the microcapsules comprise a first fragrance and a shell that surrounds said first fragrance. In some examples, the second composition may be substantially free of, or alternatively, free of a wax, an antiperspirant, and combinations thereof. In some examples, the second composition may comprise about 20% or less, about 10% or less, about 7% or less, of the microcapsules. It is to be appreciated that because the second composition is to be atomized, the concentration of the microcapsules in the second composition should not be so high as to prevent suitable atomization.

Method of Use

The compositions disclosed herein may be applied to one or more skin surfaces and/or one or more mammalian keratinous tissue surfaces as part of a user's daily routine or regimen. Additionally or alternatively, the compositions herein may be used on an "as needed" basis. The compositions may be applied to any article, such as a textile, or any absorbent article including, but not limited to, feminine hygiene articles, diapers, and adult incontinence articles. For example, while the combinations of the dispensers, assemblies, and compositions described herein are exquisitely designed to be used as a fine fragrance spray, it is understood that such combinations may also be used as a body spray, feminine spray, adult incontinence spray, baby spray, or other spray. The size, shape, and aesthetic design of the dual dispensers described herein may vary widely.

Test Methods

It is understood that the test methods that are disclosed in the Test Methods Section of the present application should be used to determine the respective values of the parameters of Applicants' invention as such invention is described and claimed herein.

(1) Fracture Strength a.) Place 1 gram of particles in 1 liter of distilled deionized (DI) water.
b.) Permit the particles to remain in the DI water for 10 minutes and then recover the particles by filtration.
c.) Determine the average rupture force of the particles by averaging the rupture force of 50 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the average fracture strength by dividing the average rupture force (in Newtons) by the average cross-sectional area of the spherical particle ($\pi r^2$, where r is the radius of the particle before compression), said average cross-sectional area being determined as follows:
  (i) Place 1 gram of particles in 1 liter of distilled deionized (DI) water.
  (ii) Permit the particles to remain in the DI water for 10 minutes and then recover the particles by filtration.
  (iii) Determine the particle size distribution of the particle sample by measuring the particle size of 50 individual particles using the experimental apparatus and method of Zhang, Z.; Sun, G; "Mechanical Properties of MelamineFormaldehyde microcapsules," J. Microencapsulation, vol 18, no. 5, pages 593-602, 2001.
  (iv) Average the 50 independent particle diameter measurements to obtain an o average particle diameter.
d.) For a capsule slurry, the sample is divided into three particle size fractions covering the particle size distribution. Per particle size fraction about 30 fracture strengths are determined.

(2) C log P

The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor, and c.A. Ramsden, Eds. P. 295, Pergamon Press, 1990, incorporated herein by reference). C log P values may be calculated by using the "C LOG P" program available from Daylight Chemical Information Systems Inc. of Irvine, Calif. U.S.A.

(3) Boiling Point

Boiling point is measured by ASTM method D2887-04a, "Standard Test Method for Boiling Range Distribution of Petroleum Fractions by Gas Chromatography," ASTM International.

(4) Volume Weight Fractions

Volume weight fractions are determined via the method of single-particle optical sensing (SPOS), also called optical particle counting (OPC). Volume weight fractions are determined via an Accusizer 780/AD supplied by Particle Sizing Systems of Santa Barbara Calif., U.S.A. or equivalent.

Procedure:
1) Put the sensor in a cold state by flushing water through the sensor;
2) Confirm background counts are less than 100 (if more than 100, continue the flush)
3) Prepare particle standard: pipette approx. 1 ml of shaken particles into a blender filled with approx. 2 cups of DI water. Blend it. Pipette approx. 1 ml of diluted, blended particles into 50 ml of DI water.
4) Measure particle standard: pipette approx. 1 ml of double diluted standard into Accusizer bulb. Press the start measurement-Autodilution button. Confirm particles counts are more than 9200 by looking in the status bar. If counts are less than 9200, press stop and 10 inject more sample.
5) Immediately after measurement, inject one full pipette of soap (5% Micro 90) into bulb and press the Start Automatic Flush Cycles button.

(5) Volume Weighted Fracture Strength (VWFS)

$$VWFS = (fracture\ strength_1 \times volume\ fraction_1) + (fracture\ strength_2 \times volume\ fraction_2) + (fracture\ strength_3 \times volume\ fraction_3)$$

Fracture strength$_1$=average fracture strength measured from a pool of 10 microcapsules (with similar particle size)
Volume fraction$_1$=volume fraction determined via Accusizer of particle distribution corresponding to fracture strength$_1$ The spread around the fracture strength to determine the volume fraction is determined as follows:

For particle batches with a mean particle sizes of about 15 micrometers a spread of about 10 micrometers is used, for particle batches with a mean particle sizes of about 30 micrometers and above, a spread of about 10 to 15 micrometers is used.

| Particle Batch | Mean Particle Size | Fracture Strength Determination at 3 particle sizes | Volume Fractions | Volume Fracture Strength |
|---|---|---|---|---|
| Melamine-based polyurea | 31 microns | 21micron, 1.8 MPa; 31 micron, 1.6 MPa; 41 micron, 1.2 MPa) | 1 to 25 microns, 30%; 25 to 36 microns, 40%; 36 to 50 microns, 30% | 1.5 MPa |

(6) Benefit Agent Leakage Test
a.) Obtain 2, one gram samples of benefit agent particle composition.
b.) Add 1 gram (Sample 1) of particle composition to 99 grams of product matrix that the particle will be employed in and with the second sample immediately proceed to Step d below.
c.) Age the particle containing product matrix (Sample 1) of a.) above for 2 weeks at 35° C. in a sealed, glass jar.
d.) Recover the particle composition's particles from the product matrix of c.) (Sample 1 in product matrix) and from particle composition (Sample 2) above by filtration.
e.) Treat each particle sample from d.) above with a solvent that will extract all the benefit agent from each samples' particles.
f.) Inject the benefit agent containing solvent from each sample from e.) above into a Gas Chromatograph and integrate the peak areas to determine the total quantity of benefit agent extracted from each sample.
g.) The benefit agent leakage is defined as:
Value from f.) above for Sample 2–Value from f.) above for Sample 1.

(7) Test Method for Determining Median Volume-Weighted Particle Size of Microcapsules One skilled in the art will recognize that various protocols may be constructed for the extraction and isolation of microcapsules from finished products, and will recognize that such methods require validation via a comparison of the resulting measured values, as measured before and after the microcapsules' addition to and extraction from the finished product. The isolated microcapsules are then formulated in deionized water to form a capsule slurry for characterization for particle size distribution.

The median volume-weighted particle size of the microcapsules is measured using an Accusizer 780A, made by Particle Sizing Systems, Santa Barbara Calif., or equivalent. The instrument is calibrated from 0 to 300 μm using particle size standards (as available from Duke/Thermo-Fisher-Scientific Inc., Waltham, Mass., USA). Samples for particle size evaluation are prepared by diluting about 1 g of capsule slurry in about 5 g of de-ionized water and further diluting about 1 g of this solution in about 25 g of water. About 1 g of the most dilute sample is added to the Accusizer and the testing initiated using the autodilution feature. The Accusizer should be reading in excess of 9200 counts/second. If the counts are less than 9200 additional sample should be added. Dilute the test sample until 9200 counts/second and then the evaluation should be initiated. After 2 minutes of testing the Accusizer will display the results, including the median volume-weighted particle size.

EXAMPLES

The following examples are given solely for the purpose of illustration and are not to be construed as limiting the invention, as many variations thereof are possible.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

Example 1

Polyacrylate Microcapsule

An oil solution, consisting of 128.4 g Fragrance Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 12.6 microns, a fracture strength of 7.68±2.0 MPa, and a 51%±20% deformation at fracture.

Example 2

Polyacrylate Microcapsules

An oil solution, consisting of 96 g Fragrance Oil, 64 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 12.6 microns, a fracture strength of 2.60±1.2 MPa, 37%±15% deformation at fracture.

Example 3

Polyacrylate Microcapsules

An oil solution, consisting of 128.4 g Fragrance Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1300-1600 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 26.1 microns, a fracture strength of 1.94±1.2 MPa, 30%±14% deformation at fracture.

Example 4

Polyacrylate Microcapsules

An oil solution, consisting of 128.4 g Fragrance Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 2500-2800 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 10.0 microns, a fracture strength of 7.64±2.2 MPa, 56%±20% deformation at fracture.

Example 5

Polyurea/urethane Microcapsules

An aqueous solution, consisting of 6.06 g Celvol 523 polyvinyl alcohol (Celanese Chemicals) and 193.94 g deionized water, is added into a temperature controlled steel jacketed reactor at room temperature. Then an oil solution, consisting of 75 g Scent A and 25 g Desmodur N3400 (polymeric hexamethylene diisocyanate), is added into the reactor. The mixture is emulsified with a propeller (4 tip, 2" diameter, flat mill blade; 2200 rpm) to desired emulsion droplet size. The resulting emulsion is then mixed with a Z-bar propeller at 450 rpm. An aqueous solution, consisting of 47 g water and 2.68 g tetraethylenepentamine, is added into the emulsion. And it is then heated to 60° C., held at 60° C. for 8 hours, and allowed to cool to room temperature. The median particle size of the resultant microcapsules is 10 microns.

Example 6

Polyurea/Urethane Microcapsules

Prepare the Oil Phase by adding 4.44 grams of isophorone diisocyanate (Sigma Aldrich) to 5.69 grams of Scent A fragrance oil. Prepare a Water Phase by mixing 1.67 grams of Ethylene Diamine (Sigma Aldrich) and 0.04 grams of 1,4-Diazabicyclo[2.2.2]octane (Sigma Aldrich) into 40 grams of a 5 wt % aqueous solution of Polyvinylpyrrolidone K-90 (Sigma Aldrich) at 10 degrees Centigrade. Next, add the Oil Phase contents to 15.0 grams of a 5 wt % aqueous solution of Polyvinylpyrrolidone K-90 (Sigma Aldrich), while agitating the mix at 1400 RPM using a Janke & Kunkel IKA Laboretechnik RW20 DZM motor with a 3-blade turbine agitator for approximately 9 minutes. Next, add the addition of the Water Phase into the emulsified Oil Phase dropwise over a 6.5 minute period, while continuing to agitate at 1400 RPM. Continue to agitate for 23 minutes, then reduce the agitation speed to 1000 RPM. After 3.75 additional hours, reduce the agitation speed to 500 RPM, and continue to agitate for 14 hours. Start heating the dispersion to 50 degrees Centigrade, over a 2 hour period. Age the capsules at 50 C for 2 hours, then collect the microcapsules. The resultant microcapsules have a median particle size of 12 microns.

Example 7

Polyacrylate Microcapsules

The polyacrylate microcapsule with the characteristics displayed in Table 3 may be prepared as follows. An oil solution, consisting of 112.34 g Fragrance Oil, 12.46 g isopropyl myristate, 2.57 g DuPont Vazo-67, 2.06 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.56 grams of tert-butyl amino ethyl methacrylate (Sigma Aldrich), 0.56 grams of beta-carboxy ethyl acrylate (Sigma Aldrich), and 46.23 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

Example 8

Spray Drying of Perfume Microcapsules

The microcapsules of Example 1 are pumped at a rate of 1 kg/hr into a co-current spray dryer (Niro Production Minor, 1.2 meter diameter) and atomized using a centrifugal wheel (100 mm diameter) rotating at 18,000 RPM. Dryer operating conditions are: air flow of 80 kg/hr, an inlet air temperature of 200 degrees Centigrade, an outlet temperature of 100 degrees Centigrade, dryer operating at a pressure of −150 millimeters of water vacuum. The dried powder is collected at the bottom of a cyclone. The collected microcapsules have an approximate particle diameter of 11 microns. The equipment used the spray drying process may be obtained from the following suppliers: IKA Werke GmbH & Co. KG, Janke and Kunkel—Str. 10, D79219 Staufen, Germany; Niro A/S Gladsaxevej 305, P.O. Box 45, 2860 Soeborg, Denmark and Watson-Marlow Bredel Pumps Limited, Falmouth, Cornwall, TR11 4RU, England.

Example 9

The microcapsules described in EXAMPLES 1-8 may be used as illustrated in the First Composition below at the indicated percentage.

| First Composition | (% w/w) |
| --- | --- |
| Ethanol (96%) | 74.88 |
| Fragrance | 14 |
| Water | 10.82 |
| Diethylamino Hydroxybenzol Hexyl Benzoate | 0.195 |
| Ethylhexyl Methoxycinnamate | 0.105 |

| Second Composition | (% w/w) |
| --- | --- |
| Water | 92.5847 |
| Microcapsules | 6.0361 |
| Carbomer | 0.5018 |
| Phenoxyethanol | 0.2509 |
| Magnesium Chloride | 0.2456 |
| Sodium Hydroxide | 0.1254 |
| Disodium EDTA | 0.0836 |
| Polyvinyl alcohol | 0.0655 |
| Sodium Benzoate | 0.0409 |
| Potassium Sorbate | 0.0409 |
| Xanthan Gum | 0.0246 |

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dual dispenser comprising a first pump in liquid communication with a first receptacle, a second pump in liquid communication with a second receptacle, and a common dispenser head, said common dispenser head comprising an output channel forming a dispensing orifice, said output channel being fed with a first and second composition coming out of the first and second pumps;
    wherein the first pump is operatively associated with a first actuating rod and the second pump is operatively associated with a second actuating rod;
    wherein the first actuating rod has a longer travel path than the second actuating rod;
    wherein the common dispenser head comprises a pivoting member which forms two support elements for simultaneously moving the two actuating rods over an axial height corresponding to the shorter travel path, the support elements then continuing their movements by pivoting/rotation of the pivoting member to finish the longer travel path;
    wherein the first receptacle comprises the first composition, the first composition comprising a volatile solvent and a first fragrance;
    wherein the second receptacle comprises the second composition, the second composition comprising a carrier and a plurality of microcapsules.

2. The dual dispenser of claim 1, wherein the two support elements are integral with each other in movement.

3. The dual dispenser of claim 1, wherein the two support elements are integral with the output channel.

4. The dual dispenser of claim 1, wherein the two support elements extend on either side of the output channel, advantageously symmetrically.

5. The dual dispenser of claim 1, wherein the two support elements pivot around the output channel.

6. The dual dispenser of claim 1, wherein the pivoting member comprises at least one thrust transmission zone, so that an axial thrust exerted on said thrust transmission zone first causes the translatory movement of the two support elements and of the output channel over the shorter travel path, then a slight rotation of the output channel around its own axis and the pivoting of the support elements to finish the longer travel path.

7. The dual dispenser of claim 6, wherein the common dispenser head comprises a cover which comes in supporting contact on the thrust transmission zones.

8. The dual dispenser of claim 7, wherein the output channel comprises a thrust transmission zone near each of the ends thereof.

9. The dual dispenser of claim 8, wherein the support elements extend substantially perpendicular to the output channel between the two thrust transmission zones.

10. The dual dispenser of claim 1, wherein the first actuating rod having the longer travel path is connected to the output channel closer to the dispensing orifice than the second actuating rod having the shorter travel path.

11. The dual dispenser of claim 1, wherein each actuating rod is topped by a cap defining a support plate for the respective support element thereof, and a connector fitting receiving a flexible conduit which connects the output channel.

12. The dual dispenser of claim 1, wherein the plurality of microcapsules encapsulate a second fragrance.

13. The dual dispenser of claim 1, wherein the microcapsules comprise a shell comprising a material selected from the group consisting of polyacrylates; polyethylenes; polyamides; polystyrenes; polyisoprenes; polycarbonates; polyesters; polyureas; polyurethanes; polyolefins; polysaccharides; epoxy resins; vinyl polymers; urea cross-linked with formaldehyde or gluteraldehyde; melamine cross-linked with formaldehyde; gelatin-polyphosphate coacervates optionally cross-linked with gluteraldehyde; gelatin-gum Arabic coacervates; cross-linked silicone fluids; polyamine reacted with polyisocyanates; acrylate monomers polymerized via free radical polymerization; silk; wool; gelatine; cellulose; proteins; and combinations thereof.

14. The dual dispenser of claim 13, wherein the microcapsules comprise a polyacrylate shell.

15. The dual dispenser of claim 1, wherein the microcapsules have a median volume-weighted particle size of from 2 microns to 80 microns, preferably from 10 microns to 30 microns, more preferably from 10 microns to 20 microns.

16. The dual dispenser of claim 1, wherein the volatile solvent comprises ethanol.

17. The dual dispenser of claim 16, wherein the first composition comprises 0.01% to 98%, by weight, of ethanol.

18. The dual dispenser of claim 1, wherein the carrier comprises water.

19. The dual dispenser of claim 18, wherein the second composition comprises from 5% to 95%, by weight, of water.

20. The dual dispenser of claim 1, wherein at least one of the compositions is free of a propellant.

21. The dual dispenser of claim 1, wherein at least one of the compositions further comprises a coloring agent.

22. The dual dispenser of claim 1, wherein the second composition further comprises a suspending agent.

23. The dual dispenser of claim 1, wherein the second composition further comprises from 5% to 90%, of a cross-linked polyacrylate polymer.

24. The dual dispenser of claim 1, wherein the second composition is substantially free of a material selected from the group consisting of a propellant, ethanol, a detersive surfactant, and combinations thereof; preferably free of a material selected from the group consisting of a propellant, ethanol, a detersive surfactant, and combinations thereof.

25. The dual dispenser of claim 1, wherein the first composition is substantially free of a material selected from the group consisting of a propellant, microcapsules, a detersive surfactant, and combinations thereof; preferably free of a material selected from the group consisting of propellant, microcapsules, a detersive surfactant, and combinations thereof.

26. The dual dispenser of claim 1, wherein the carrier is water and the second composition comprises from about 0.1% to about 95% by weight of the second composition of the water.

27. A method of providing a longer lasting fragrance, the method comprising spraying the first and second composition using the dual dispenser of claim 1.

\* \* \* \* \*